United States Patent
Heliker et al.

(10) Patent No.: US 10,545,845 B1
(45) Date of Patent: *Jan. 28, 2020

(54) MESH NETWORK ROUTING BASED ON AVAILABILITY OF ASSETS

(71) Applicant: Uptake Technologies, Inc., Chicago, IL (US)

(72) Inventors: Brett Heliker, Chicago, IL (US); Brad Nicholas, Wheaton, IL (US)

(73) Assignee: Uptake Technologies, Inc., Chicago, IL (US)

( * ) Notice: Subject to any disclaimer, the term of this patent is extended or adjusted under 35 U.S.C. 154(b) by 73 days.

This patent is subject to a terminal disclaimer.

(21) Appl. No.: 15/805,124

(22) Filed: Nov. 6, 2017

Related U.S. Application Data

(63) Continuation of application No. 14/853,189, filed on Sep. 14, 2015, now Pat. No. 9,842,034.

(51) Int. Cl.
| | | |
|---|---|---|
| *G06F 11/26* | (2006.01) | |
| *G06F 11/07* | (2006.01) | |
| *G06F 11/00* | (2006.01) | |
| *G06F 11/263* | (2006.01) | |
| *G06Q 10/06* | (2012.01) | |
| *G08B 21/18* | (2006.01) | |
| *G06Q 10/00* | (2012.01) | |

(52) U.S. Cl.
CPC ............ *G06F 11/26* (2013.01); *G06F 11/008* (2013.01); *G06F 11/0709* (2013.01); *G06F 11/079* (2013.01); *G06F 11/0751* (2013.01); *G06F 11/0772* (2013.01); *G06F 11/0787* (2013.01); *G06F 11/0793* (2013.01); *G06F 11/263* (2013.01); *G06Q 10/0633* (2013.01); *G06Q 10/20* (2013.01); *G08B 21/18* (2013.01)

(58) Field of Classification Search
CPC ........................................................ G06F 11/26
See application file for complete search history.

(56) References Cited

U.S. PATENT DOCUMENTS

| 5,566,092 A | 10/1996 | Wang et al. |
| 5,633,800 A | 5/1997 | Bankert et al. |

(Continued)

FOREIGN PATENT DOCUMENTS

| JP | 2013239827 | 11/2013 |
| WO | 2011117570 | 9/2011 |

(Continued)

OTHER PUBLICATIONS

European Patent Office Extended Search Report for EP Application No. 16847112.6 dated Jan. 23, 2019, 7 pages.

(Continued)

*Primary Examiner* — Albert T Chou
(74) *Attorney, Agent, or Firm* — Lee Sullivan Shea & Smith LLP

(57) ABSTRACT

Disclosed herein are systems, devices, and methods related to assets and predictive models and corresponding workflows that are related to updating a routing table. In particular, examples involve based on a predictive model, determining that a given asset of a plurality of assets in a mesh network is likely to be unavailable within a given period of time in the future and in response to the determining, causing a routing configuration for at least one other asset in the mesh network to be updated.

20 Claims, 8 Drawing Sheets

(56) References Cited

U.S. PATENT DOCUMENTS

| | | |
|---|---|---|
| 6,256,594 B1 | 7/2001 | Yamamoto et al. |
| 6,336,065 B1 | 1/2002 | Gibson et al. |
| 6,353,902 B1 | 3/2002 | Kulatunge et al. |
| 6,442,542 B1 | 8/2002 | Ramani et al. |
| 6,473,659 B1 | 10/2002 | Shah et al. |
| 6,622,264 B1 | 9/2003 | Bliley et al. |
| 6,634,000 B1 | 10/2003 | Jammu et al. |
| 6,643,600 B2 | 11/2003 | Yanosik et al. |
| 6,650,949 B1 | 11/2003 | Fera et al. |
| 6,725,398 B1 | 4/2004 | Varma et al. |
| 6,760,631 B1 | 7/2004 | Berkowitz et al. |
| 6,775,641 B2 | 8/2004 | Wegerich et al. |
| 6,799,154 B1 | 9/2004 | Aragones et al. |
| 6,823,253 B2 | 11/2004 | Brunell |
| 6,859,739 B2 | 2/2005 | Wegerich et al. |
| 6,892,163 B1 | 5/2005 | Herzog et al. |
| 6,947,797 B2 | 9/2005 | Dean et al. |
| 6,952,662 B2 | 10/2005 | Wegerich et al. |
| 6,957,172 B2 | 10/2005 | Wegerich |
| 6,975,962 B2 | 12/2005 | Wegerich et al. |
| 7,020,595 B1 | 3/2006 | Adibhatla et al. |
| 7,082,379 B1 | 7/2006 | Bickford et al. |
| 7,100,084 B2 | 8/2006 | Unkle et al. |
| 7,107,491 B2 | 9/2006 | Graichen et al. |
| 7,127,371 B2 | 10/2006 | Duckert et al. |
| 7,233,886 B2 | 6/2007 | Wegerich et al. |
| 7,280,941 B2 | 10/2007 | Bonanni et al. |
| 7,308,385 B2 | 12/2007 | Wegerich et al. |
| 7,373,283 B2 | 5/2008 | Herzog et al. |
| 7,403,869 B2 | 7/2008 | Wegerich et al. |
| 7,409,320 B2 | 8/2008 | Wegerich |
| 7,415,382 B1 | 8/2008 | Bickford et al. |
| 7,428,478 B2 | 9/2008 | Aragones |
| 7,447,666 B2 | 11/2008 | Wang |
| 7,457,693 B2 | 11/2008 | Olsen et al. |
| 7,457,732 B2 | 11/2008 | Aragones et al. |
| 7,509,235 B2 | 3/2009 | Bonissone et al. |
| 7,536,364 B2 | 5/2009 | Subbu et al. |
| 7,539,597 B2 | 5/2009 | Wegerich et al. |
| 7,548,830 B2 | 6/2009 | Goebel et al. |
| 7,634,384 B2 | 12/2009 | Eryurek et al. |
| 7,640,145 B2 | 12/2009 | Wegerich et al. |
| 7,660,705 B1 | 2/2010 | Meek et al. |
| 7,725,293 B2 | 5/2010 | Bonissone et al. |
| 7,739,096 B2 | 6/2010 | Wegerich et al. |
| 7,756,678 B2 | 7/2010 | Bonissone et al. |
| 7,822,578 B2 | 10/2010 | Kasztenny et al. |
| 7,869,908 B2 | 1/2011 | Walker |
| 7,919,940 B2 | 4/2011 | Miller et al. |
| 7,941,701 B2 | 5/2011 | Wegerich et al. |
| 7,962,240 B2 | 6/2011 | Morrison et al. |
| 8,024,069 B2 | 9/2011 | Miller et al. |
| 8,050,800 B2 | 11/2011 | Miller et al. |
| 8,145,578 B2 | 3/2012 | Pershing et al. |
| 8,229,769 B1 | 7/2012 | Hopkins |
| 8,234,420 B2 | 7/2012 | Lueckenbach et al. |
| 8,239,170 B2 | 8/2012 | Wegerich |
| 8,275,577 B2 | 9/2012 | Herzog |
| 8,285,402 B2 | 10/2012 | Lueckenbach et al. |
| 8,311,774 B2 | 11/2012 | Hines |
| 8,352,216 B2 | 1/2013 | Subbu et al. |
| 8,532,795 B2 | 9/2013 | Adavi et al. |
| 8,533,018 B2 | 9/2013 | Miwa et al. |
| 8,560,494 B1 | 10/2013 | Downing et al. |
| 8,620,618 B2 | 12/2013 | Eryurek et al. |
| 8,620,853 B2 | 12/2013 | Herzog |
| 8,626,385 B2 | 1/2014 | Humphrey |
| 8,645,276 B2 | 2/2014 | Wong et al. |
| 8,660,980 B2 | 2/2014 | Herzog |
| 8,689,108 B1 | 4/2014 | Duffield et al. |
| 8,713,467 B1 | 4/2014 | Goldenberg et al. |
| 8,786,605 B1 | 7/2014 | Curtis et al. |
| 8,799,799 B1 | 8/2014 | Cervelli et al. |
| 8,812,960 B1 | 8/2014 | Sun et al. |
| 8,832,594 B1 | 9/2014 | Thompson et al. |
| 8,850,000 B2 | 9/2014 | Collins et al. |
| 8,862,938 B2 | 10/2014 | Souvannarath |
| 8,868,537 B1 | 10/2014 | Colgrove et al. |
| 8,886,601 B1 | 11/2014 | Landau et al. |
| 8,909,656 B2 | 12/2014 | Kumar et al. |
| 8,917,274 B2 | 12/2014 | Ma et al. |
| 8,918,246 B2 | 12/2014 | Friend |
| 8,924,429 B1 | 12/2014 | Fisher et al. |
| 8,935,201 B1 | 1/2015 | Fisher et al. |
| 8,937,619 B2 | 1/2015 | Sharma et al. |
| 8,938,686 B1 | 1/2015 | Erenrich et al. |
| 9,842,034 B2 * | 12/2017 | Heliker ............... G06F 11/0751 |
| 2002/0091972 A1 | 7/2002 | Harris et al. |
| 2002/0152056 A1 | 10/2002 | Herzog et al. |
| 2003/0055666 A1 | 3/2003 | Roddy et al. |
| 2003/0126258 A1 | 7/2003 | Conkright et al. |
| 2004/0181712 A1 | 9/2004 | Taniguchi et al. |
| 2004/0243636 A1 | 12/2004 | Hasiewicz et al. |
| 2005/0119905 A1 | 6/2005 | Wong et al. |
| 2005/0222747 A1 | 10/2005 | Vhora et al. |
| 2006/0062199 A1 | 3/2006 | Yoshizawa |
| 2007/0174449 A1 | 7/2007 | Gupta |
| 2007/0263628 A1 | 11/2007 | Axelsson et al. |
| 2008/0059080 A1 | 3/2008 | Greiner et al. |
| 2008/0059120 A1 | 3/2008 | Xiao et al. |
| 2009/0146839 A1 | 6/2009 | Reddy et al. |
| 2010/0188239 A1 | 7/2010 | Rockwell |
| 2012/0026890 A1 | 2/2012 | Banka et al. |
| 2012/0271612 A1 | 10/2012 | Barsoum et al. |
| 2012/0310597 A1 | 12/2012 | Uchiyama et al. |
| 2013/0010610 A1 | 1/2013 | Karthikeyan et al. |
| 2013/0024416 A1 | 1/2013 | Herzog |
| 2013/0283773 A1 | 10/2013 | Hague |
| 2013/0325502 A1 | 12/2013 | Robicsek et al. |
| 2014/0012886 A1 | 1/2014 | Downing et al. |
| 2014/0032132 A1 | 1/2014 | Stratton et al. |
| 2014/0060030 A1 | 3/2014 | Ma et al. |
| 2014/0089035 A1 | 3/2014 | Jericho et al. |
| 2014/0098658 A1 | 4/2014 | Johansen |
| 2014/0105481 A1 | 4/2014 | Hasselbusch et al. |
| 2014/0121868 A1 | 5/2014 | Zhang et al. |
| 2014/0169398 A1 | 6/2014 | Arndt et al. |
| 2014/0170617 A1 | 6/2014 | Johnson et al. |
| 2014/0184643 A1 | 7/2014 | Friend |
| 2014/0222355 A1 | 8/2014 | Cheim et al. |
| 2014/0286301 A1 | 9/2014 | Werb et al. |
| 2014/0330600 A1 | 11/2014 | Candas et al. |
| 2014/0330749 A1 | 11/2014 | Candas et al. |
| 2014/0351642 A1 | 11/2014 | Bates et al. |
| 2014/0357295 A1 | 12/2014 | Skomra et al. |
| 2014/0358601 A1 | 12/2014 | Smiley et al. |
| 2015/0046870 A1 | 2/2015 | Goldenberg et al. |
| 2015/0063159 A1 | 3/2015 | Bonawitz et al. |
| 2015/0195192 A1 | 7/2015 | Vasseur et al. |
| 2015/0262060 A1 | 9/2015 | Husain et al. |

FOREIGN PATENT DOCUMENTS

| | | |
|---|---|---|
| WO | 2013034420 | 3/2013 |
| WO | 2014145977 | 9/2014 |
| WO | 2014205497 | 12/2014 |

OTHER PUBLICATIONS

Biswas, "Redundancy-based Approaches in Wireless Multihop Network Design", PhD Dissertation Submitted to Graduate Faculty of North Carolina State University (2014).

Isermann, "Model-based Fault Detection and Diagnosis—Status and Applications", Institute of Automatic Control, Darmstadt University of Technology (2004).

Narasimhan et al, "Combining Model-Based and Feature-Driven Diagnosis Approaches—A Case Study on Electromechanical Actuators", 21st International Workshop on Principles of Diagnosis (2010).

Prentzas et al, Categorizing Approaches Combining Rule-Based and Case-Based Reasoning.

Infor M3 Enterprise Management System, Infor.com (2014).

(56) References Cited

OTHER PUBLICATIONS

Infor Equipment, Infor.com (2012).
Infor Introduces Next-Generation Solution for Equipment Dealers and Service Providers, Infor.com (Feb. 20, 2014).
Infor Equipment for Rental, Infor.com (2013).
Waltermire et al, Applying the Continuous Monitoring Technical Reference Model to the Asset, Configuration, and Vulnerability Management Domains (Draft), NIST (Jan. 2012).
"P. Brown. ""Standard Based Integration Specification: Common Information Model Framework for Asset Health Data Exchange."" http://www.epri.combabstracts/pages/productabstract.aspx?ProductId= 000000003002002586. Dec. 16, 2014".
"International Searching Authority, Written Opinion dated Dec. 14, 2016, issued in connection with International Application No. PCT/US2016/051387, filed on Sep. 12, 2016, 5 pages."
"International Search Report for Application No. PCT/US2016/051387, dated Dec. 14, 2016, 3 pages".

\* cited by examiner

MESH NETWORK ROUTING BASED ON AVAILABILITY OF ASSETS

CROSS REFERENCE TO RELATED APPLICATIONS

This application is a continuation of, and claims priority to, U.S. Non-Provisional patent application Ser. No. 14/853,189, filed on Sep. 14, 2015, entitled "Mesh Network Routing Based on Availability of Assets," which is incorporated herein by reference in its entirety.

This application also incorporates by reference U.S. Non-Provisional patent application Ser. No. 14/732,258, filed on Jun. 5, 2015, entitled "Asset Health Score" and U.S. Non-Provisional patent application Ser. No. 14/744,352, filed on Jun. 19, 2015, entitled "Aggregate Predictive Model & Workflow for Local Execution," each of which is incorporated in its entirety.

BACKGROUND

Today, machines (also referred to herein as "assets") are ubiquitous in many industries. From locomotives that transfer cargo across countries to medical equipment that helps nurses and doctors to save lives, assets serve an important role in everyday life. Depending on the role that an asset serves, its complexity, and cost, may vary. For instance, some assets may include multiple subsystems that must operate in harmony for the asset to function properly (e.g., an engine, transmission, etc. of a locomotive).

Because of the key role that assets play in everyday life, it is desirable for assets to be repairable with limited downtime. Accordingly, some have developed mechanisms to monitor and detect abnormal conditions within an asset to facilitate repairing the asset, perhaps with minimal downtime.

OVERVIEW

The current approach for monitoring assets generally involves an on-asset computer that receives signals from various sensors distributed throughout an asset that monitor the operating conditions of the asset. As one representative example, if the asset is a locomotive, the sensors may monitor parameters such as temperatures, voltages, and speeds, among other examples. If sensor signals from one or more sensors reach certain values, the on-asset computer may then generate an abnormal-condition indicator, such as a "fault code," which is an indication that an abnormal condition has occurred within the asset.

In general, an abnormal condition may be a defect at an asset or component thereof, which may lead to a failure of the asset and/or component. As such, an abnormal condition may be associated with a given failure, or perhaps multiple failures, in that the abnormal condition is symptomatic of the given failure or failures. In practice, a user typically defines the sensors and respective sensor values associated with each abnormal-condition indicator. That is, the user defines an asset's "normal" operating conditions (e.g., those that do not trigger fault codes) and "abnormal" operating conditions (e.g., those that trigger fault codes).

After the on-asset computer generates an abnormal-condition indicator, the indicator and/or sensor signals may be passed to a remote location where a user may receive some indication of the abnormal condition and/or sensor signals and decide whether to take action. One action that the user might take is to assign a mechanic or the like to evaluate and potentially repair the asset. Once at the asset, the mechanic may connect a computing device to the asset and operate the computing device to cause the asset to utilize one or more local diagnostic tools to facilitate diagnosing the cause of the generated indicator.

While current asset-monitoring systems are generally effective at triggering abnormal-condition indicators, such systems are typically reactionary. That is, by the time the asset-monitoring system triggers an indicator, a failure within the asset may have already occurred (or is right about to occur), which may lead to costly downtime, among other disadvantages. Additionally, due to the simplistic nature of on-asset abnormality-detection mechanisms in such asset-monitoring systems, current asset-monitoring approaches tend to involve a remote computing system performing monitoring computations for an asset and then transmitting instructions to the asset if a problem is detected. This may be disadvantageous due to network latency and/or infeasible when the asset moves outside of coverage of a communication network.

Assets at a site may be formed into mesh networks for certain purposes. For example, a job construction site may include assets that communicate information with each other, such as location data, status data, etc. The mesh network may provide a cheap and reliable way to enable communication between the assets. Each asset in the mesh network may use a routing configuration to determine one or more paths for data to travel in the mesh network. For example, a first asset may determine whether to transmit data to a second asset or a third asset depending on various factors including a shortest latency, a shortest distance, a minimum travel time, a minimum energy expenditure, etc. The routing configuration may include different data structures for storing the one or more paths including a routing table.

One or more assets in the mesh network may use a communication network to transmit the data outside the mesh network to a remote computing system. This asset may be known as a "gateway" because the asset provides the assets in the mesh network with access to additional network resources.

The assets in the mesh network include sensors that generate sensor data. The assets may transmit the sensor data to the remote computing system by accessing the communication network if the assets are gateways or by transmitting the sensor data to the gateway.

The remote system defines a predictive model and corresponding workflow (referred to herein as a "model-workflow pair") that are related to the operation of the assets. The predictive model may be executed either at the remote system itself or can be executed locally by the assets. For example, the assets may be configured to receive the model-workflow pair and utilize a local analytics device to operate in accordance with the model-workflow pair.

Generally, a model-workflow pair may cause an asset to monitor certain operating conditions and when certain conditions exist, modify a behavior that may help facilitate preventing an occurrence of a particular event. Specifically, a predictive model may receive as inputs sensor data from a particular set of asset sensors and output a likelihood that a given asset will be unavailable within a given period of time in the future. A workflow may involve one or more operations that are performed based on the likelihood of the one or more particular events that is output by the model.

In practice, the remote computing system may define an aggregate, predictive model and corresponding workflows, individualized, predictive models and corresponding workflows, or some combination thereof. An "aggregate" model/workflow may refer to a model/workflow that is generic for a group of assets, while an "individualized" model/workflow may refer to a model/workflow that is tailored for a single asset or subgroup of assets from the group of assts.

In accordance with this disclosure, one specific model-workflow pair can be a predictive failure model that triggers a workflow for causing the mesh network's routing table to be updated. This model-workflow pair may be executed at the remote computing system (in which case the remote computing system will instruct the assets in the mesh to update their respective routing tables) or may be executed locally at an asset itself (in which case the asset would instruct the other assets in the mesh to update the tables).

The predictive failure model may take various forms, one example of which is a health score model where the predictive failure model monitors the health of an asset and outputs a health metric (e.g., "health score") for an asset, which is a single, aggregated metric that indicates whether a failure will occur at a given asset (and thus whether the given asset will become unavailable) within a given timeframe into the future. In particular, a health metric may indicate a likelihood that no failures from a group of failures will occur at an asset within a given timeframe into the future, or a health metric may indicate a likelihood that at least one failure from a group of failures will occur at an asset within a given timeframe into the future. The workflow for causing the routing table to be updated may take various forms, one example of which is a workflow triggered when the heath score falls below a certain threshold.

Once it is determined that a given asset is likely to be unavailable within a given time in the future, a routing configuration for at least one other asset in the mesh network is updated. For example, the remote computing system may transmit a determination that the given asset is likely to be unavailable within the given period of time in the future to one of the plurality of assets in the mesh network. That asset may then update its routing configuration and transmit the determination to another asset in the mesh network. In another example, the remote computing system may send to one or more assets in the mesh network a corresponding updated routing configuration.

The example systems, devices, and methods disclosed herein seek to help address one or more of these issues. In example implementations, a network configuration may include a communication network that facilitates communications between assets and a remote computing system.

One of ordinary skill in the art will appreciate these as well as numerous other aspects in reading the following disclosure.

DETAILED DESCRIPTION

The following disclosure makes reference to the accompanying figures and several exemplary scenarios. One of ordinary skill in the art will understand that such references are for the purpose of explanation only and are therefore not meant to be limiting. Part or all of the disclosed systems, devices, and methods may be rearranged, combined, added to, and/or removed in a variety of manners, each of which is contemplated herein.

I. Example Network Configuration

Figure 1:
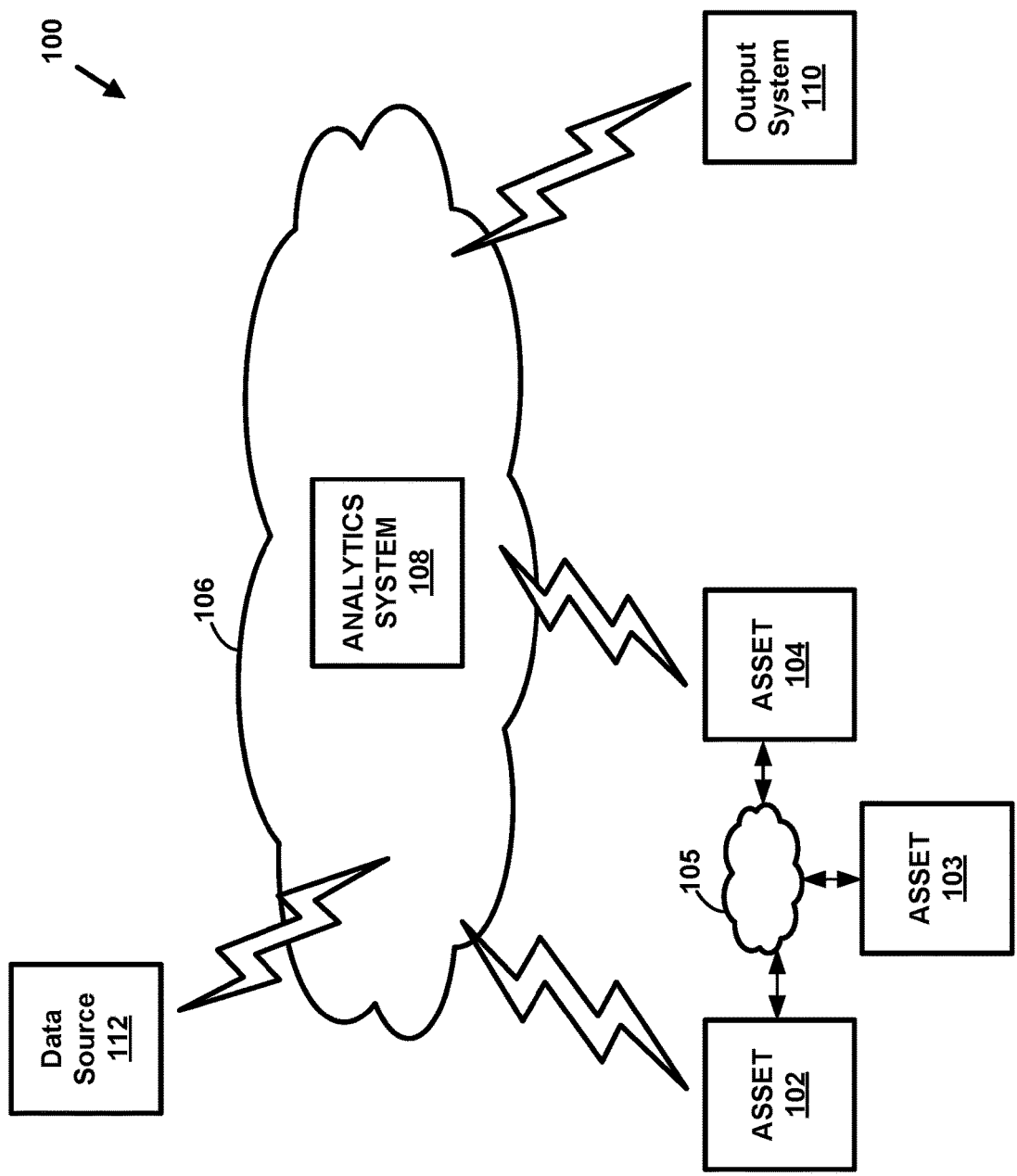
FIG. 1 depicts an example network configuration in which example embodiments may be implemented.

Turning now to the figures, FIG. 1 depicts an example network configuration 100 in which example embodiments may be implemented. As shown, the network configuration 100 includes at least three assets 102, 103, and 104 coupled in a mesh network 105, a communication network 106, a remote computing system 108 that may take the form of an analytics system, an output system 110, and a data source 112.

The communication network 106 may communicatively connect each of the components in the network configuration 100. For instance, the assets 102, 103, and 104 may communicate with the analytics system 108 via the communication network 106. The assets 102, 103, and 104 may communicate with each other via the mesh network 105. The assets 102, 103, and 104 may also communicate with the analytics system 108 by communicating via the mesh network 105 and via the communication network 106. For example, asset 102 may transmit sensor data to asset 103, which transmits the sensor data to the analytics system 108 via the communication network. In addition, the mesh network 105 may be configured so that a subset of the assets 102, 103, and 104 communicate with the analytics system 108. For example, asset 103 may be the only asset that communicates with the analytics system 108 while assets 102, 103, and 104 communicate only with other assets 103 and 104 or 102 and 103, respectively, in the mesh network 105.

In some cases, the assets 102, 103, and 104 may communicate with one or more intermediary systems, such as an asset gateway (not pictured), that in turn communicates with the analytics system 108. Likewise, the analytics system 108 may communicate with the output system 110 via the communication network 106. In some cases, the analytics system 108 may communicate with one or more intermediary systems, such as a host server (not pictured), that in turn communicates with the output system 110. Many other configurations are also possible.

In general, the assets 102, 103, and 104 may take the form of any device configured to perform one or more operations (which may be defined based on the field) and may also include equipment configured to transmit data indicative of one or more operating conditions of the given asset. In some examples, an asset may include one or more subsystems configured to perform one or more respective operations. In practice, multiple subsystems may operate in parallel or sequentially in order for an asset to operate.

Example assets may include transportation machines (e.g., locomotives, aircraft, semi-trailer trucks, ships, etc.), industrial machines (e.g., mining equipment, construction equipment, processing equipment, assembly equipment, etc.), medical machines (e.g., medical imaging equipment, surgical equipment, medical monitoring systems, medical laboratory equipment, etc.), utility machines (e.g., turbines, solar farms, etc.), and unmanned aerial vehicles, among other examples. Those of ordinary skill in the art will appreciate that these are but a few examples of assets and that numerous others are possible and contemplated herein.

In example implementations, the assets 102, 103, and 104 may each be of the same type (e.g., a fleet of locomotives or aircraft, a group of wind turbines, a pool of milling machines, or a set of magnetic resonance imagining (MM) machines, among other examples) and perhaps may be of the same class (e.g., same equipment type, brand, and/or model). In other examples, the assets 102, 103, and 104 may differ by type, by brand, by model, etc. For example, assets 102, 103, and 104 may be different pieces of equipment at a job site (e.g., an excavation site) or a production facility, among numerous other examples. The assets are discussed in further detail below with reference to FIG. 2.

As shown, the assets 102, 103, and 104, and perhaps the data source 112, may communicate with the analytics system 108 via the communication network 106 and/or the mesh network 105. In general, the communication network 106 may include one or more computing systems and network infrastructure configured to facilitate transferring data between network components. The communication network 106 may be or may include one or more Wide-Area Networks (WANs) and/or Local-Area Networks (LANs), which may be wired and/or wireless and may feature varying degrees of bandwidth, power consumption, and/or latency characteristics. In some examples, the communication network 106 may include one or more cellular or satellite networks and/or the Internet, among other networks. The communication network 106 may operate according to one or more communication protocols, such as LTE, CDMA, GSM, WiFi, LPWAN, Bluetooth, Ethernet, HTTP/S, TCP, CoAP/DTLS and the like. Although the communication network 106 is shown as a single network, it should be understood that the communication network 106 may include multiple, distinct networks that are themselves communicatively linked. The communication network 106 could take other forms as well.

In general, the mesh network 105 may take the form of a network topology where the assets 102, 103, and 104 (and potentially other network elements) serve as "nodes" that are configured to facilitate routing data from a source (e.g., the analytics system 108) to a destination (e.g., the asset 103). For example, the analytics system 108 may transmit data destined for the asset 103 via the asset 104 that relays the data to the asset 103. Similarly, the asset 103 may transmit data destined for the analytics system 108 via the asset 102 that relays the data to the analytics system 108 via the communication network 106. Other examples of data routing are also possible. Mesh networks are discussed in further detail below with respect to FIG. 4.

As noted above, the analytics system 108 may be configured to receive data from the assets 102, 103, and 104 and the data source 112. Broadly speaking, the analytics system 108 may include one or more computing systems, such as servers and databases, configured to receive, process, analyze, and output data. The analytics system 108 may be configured according to a given dataflow technology, such as TPL Dataflow or NiFi, among other examples. The analytics system 108 is discussed in further detail below with reference to FIG. 3.

As shown, the analytics system 108 may be configured to transmit data to the assets 102, 103, and 104 and/or to the output system 110. The particular data transmitted may take various forms and will be described in further detail below.

In general, the output system 110 may take the form of a computing system or device configured to receive data and provide some form of output. The output system 110 may take various forms. In one example, the output system 110 may be or include an output device configured to receive data and provide an audible, visual, and/or tactile output in response to the data. In general, an output device may include one or more input interfaces configured to receive user input, and the output device may be configured to transmit data through the communication network 106 based on such user input. Examples of output devices include tablets, smartphones, laptop computers, other mobile computing devices, desktop computers, smart televisions, and the like.

Another example of the output system 110 may take the form of a work-order system configured to output a request for a mechanic or the like to repair an asset. Yet another example of the output system 110 may take the form of a parts-ordering system configured to place an order for a part of an asset and output a receipt thereof. Numerous other output systems are also possible.

The data source 112 may be configured to communicate with the analytics system 108. In general, the data source 112 may be or include one or more computing systems configured to collect, store, and/or provide to other systems, such as the analytics system 108, data that may be relevant to the functions performed by the analytics system 108. The data source 112 may be configured to generate and/or obtain data independently from the assets 102, 103, and 104. As such, the data provided by the data source 112 may be referred to herein as "external data." The data source 112 may be configured to provide current and/or historical data. In practice, the analytics system 108 may receive data from the data source 112 by "subscribing" to a service provided by the data source. However, the analytics system 108 may receive data from the data source 112 in other manners as well.

Examples of the data source 112 include environment data sources, asset-management data sources, and other data sources. In general, environment data sources provide data indicating some characteristic of the environment in which assets are operated. Examples of environment data sources include weather-data servers, global navigation satellite systems (GNSS) servers, map-data servers, and topography-data servers that provide information regarding natural and artificial features of a given area, among other examples.

In general, asset-management data sources provide data indicating events or statuses of entities (e.g., other assets) that may affect the operation or maintenance of assets (e.g., when and where an asset may operate or receive maintenance). Examples of asset-management data sources include traffic-data servers that provide information regarding air, water, and/or ground traffic, asset-schedule servers that provide information regarding expected routes and/or locations of assets on particular dates and/or at particular times, defect detector systems (also known as "hotbox" detectors) that provide information regarding one or more operating conditions of an asset that passes in proximity to the defect detector system, part-supplier servers that provide information regarding parts that particular suppliers have in stock and prices thereof, and repair-shop servers that provide information regarding repair shop capacity and the like, among other examples.

Examples of other data sources include power-grid servers that provide information regarding electricity consumption and external databases that store historical operating data for assets, among other examples. One of ordinary skill in the art will appreciate that these are but a few examples of data sources and that numerous others are possible.

It should be understood that the network configuration 100 is one example of a network in which embodiments described herein may be implemented. Numerous other arrangements are possible and contemplated herein. For instance, other network configurations may include additional components not pictured and/or more or less of the pictured components.

II. Example Asset

Figure 2:
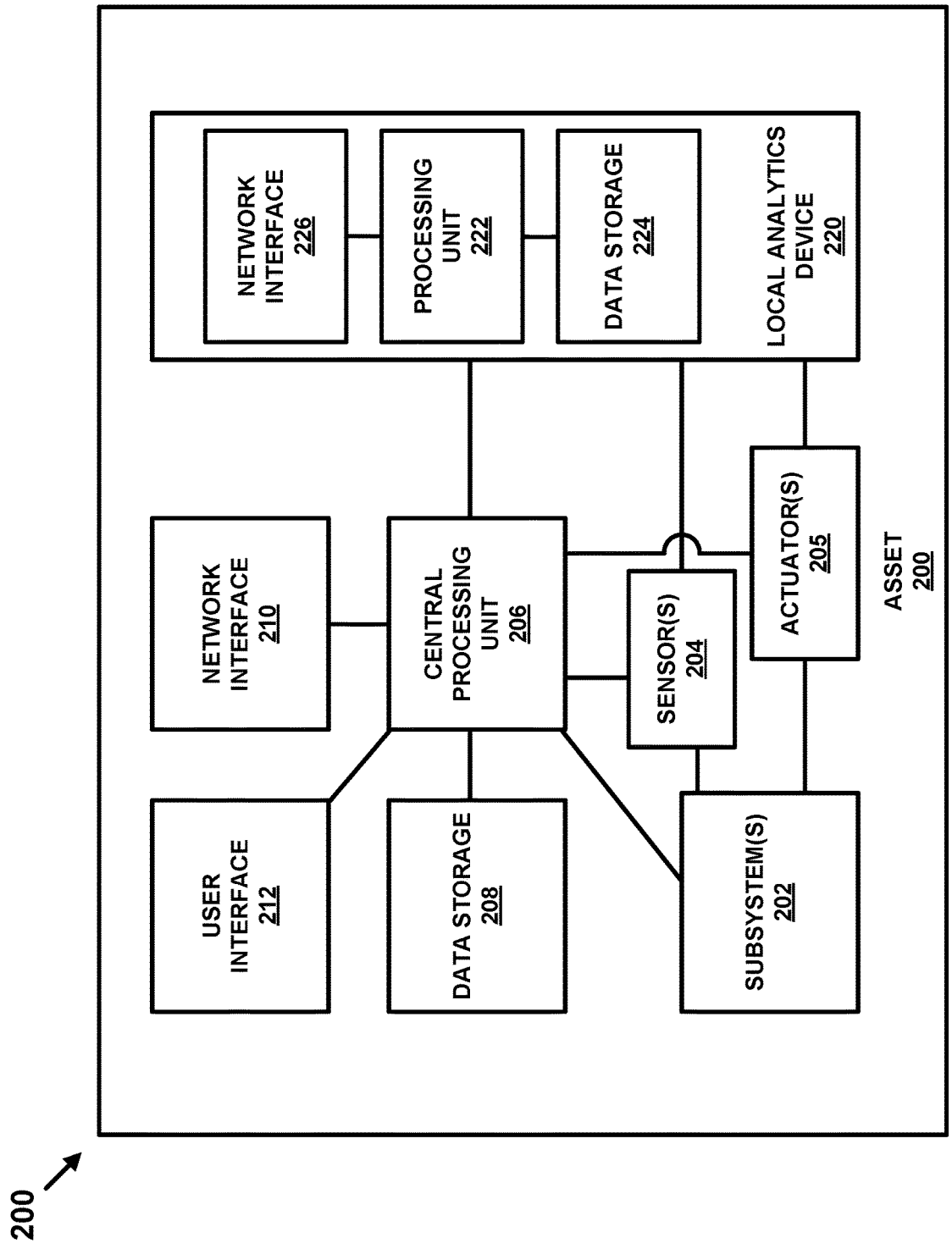
FIG. 2 depicts a simplified block diagram of an example asset.

Turning to FIG. 2, a simplified block diagram of an example asset 200 is depicted. One or more of assets 102, 103, and 104 from FIG. 1 may be configured like the asset 200. As shown, the asset 200 may include one or more subsystems 202, one or more sensors 204, one or more actuators 205, a central processing unit 206, data storage 208, a network interface 210, a user interface 212, and perhaps also a local analytics device 220, all of which may be communicatively linked by a system bus, network, or other connection mechanism. One of ordinary skill in the art will appreciate that the asset 200 may include additional components not shown and/or more or less of the depicted components.

Broadly speaking, the asset 200 may include one or more electrical, mechanical, and/or electromechanical components configured to perform one or more operations. In some cases, one or more components may be grouped into a given subsystem 202.

Generally, a subsystem 202 may include a group of related components that are part of the asset 200. A single subsystem 202 may independently perform one or more operations or the single subsystem 202 may operate along with one or more other subsystems to perform one or more operations. Typically, different types of assets, and even different classes of the same type of assets, may include different subsystems.

For instance, in the context of transportation assets, examples of subsystems 202 may include engines, transmissions, drivetrains, fuel systems, battery systems, exhaust systems, braking systems, electrical systems, signal processing systems, generators, gear boxes, rotors, and hydraulic systems, among numerous other subsystems. In the context of a medical machine, examples of subsystems 202 may include scanning systems, motors, coil and/or magnet systems, signal processing systems, rotors, and electrical systems, among numerous other subsystems.

As suggested above, the asset 200 may be outfitted with various sensors 204 that are configured to monitor operating conditions of the asset 200 and various actuators 205 that are configured to interact with the asset 200 or a component thereof and monitor operating conditions of the asset 200. In some cases, some of the sensors 204 and/or actuators 205 may be grouped based on a particular subsystem 202. In this way, the group of sensors 204 and/or actuators 205 may be configured to monitor operating conditions of the particular subsystem 202, and the actuators from that group may be configured to interact with the particular subsystem 202 in some way that may alter the subsystem's behavior based on those operating conditions.

In general, a sensor 204 may be configured to detect a physical property, which may be indicative of one or more operating conditions of the asset 200, and provide an indication, such as an electrical signal, of the detected physical property. In operation, the sensors 204 may be configured to obtain measurements continuously, periodically (e.g., based on a sampling frequency), and/or in response to some triggering event. In some examples, the sensors 204 may be preconfigured with operating parameters for performing measurements and/or may perform measurements in accordance with operating parameters provided by the central processing unit 206 (e.g., sampling signals that instruct the sensors 204 to obtain measurements). In examples, different sensors 204 may have different operating parameters (e.g., some sensors may sample based on a first frequency, while other sensors sample based on a second, different frequency). In any event, the sensors 204 may be configured to transmit electrical signals indicative of a measured physical property to the central processing unit 206. The sensors 204 may continuously or periodically provide such signals to the central processing unit 206.

For instance, sensors 204 may be configured to measure physical properties such as the location and/or movement of the asset 200, in which case the sensors may take the form of GNSS sensors, dead-reckoning-based sensors, accelerometers, gyroscopes, pedometers, magnetometers, or the like.

Additionally, various sensors 204 may be configured to measure other operating conditions of the asset 200, examples of which may include temperatures, pressures, speeds, friction, power usages, fuel usages, fluid levels, runtimes, voltages and currents, magnetic fields, electric fields, and power generation, among other examples. One of ordinary skill in the art will appreciate that these are but a few example operating conditions that sensors may be configured to measure. Additional or fewer sensors may be used depending on the industrial application or specific asset.

As suggested above, an actuator 205 may be configured similar in some respects to a sensor 204. Specifically, an actuator 205 may be configured to detect a physical property indicative of an operating condition of the asset 200 and provide an indication thereof in a manner similar to the sensor 204.

Moreover, an actuator 205 may be configured to interact with the asset 200, one or more subsystems 202, and/or some component thereof. As such, an actuator 205 may include a motor or the like that is configured to move or otherwise control a component or system. In a particular example, an actuator may be configured to measure a fuel flow and alter the fuel flow (e.g., restrict the fuel flow), or an actuator may be configured to measure a hydraulic pressure and alter the hydraulic pressure (e.g., increase or decrease the hydraulic pressure). Numerous other example interactions of an actuator are also possible and contemplated herein.

Generally, the central processing unit 206 may include one or more processors and/or controllers, which may take the form of a general- or special-purpose processor or controller. In particular, in example implementations, the central processing unit 206 may be or include microprocessors, microcontrollers, application specific integrated circuits, digital signal processors, and the like. In turn, the data storage 208 may be or include one or more non-transitory computer-readable storage media, such as optical, magnetic, organic, or flash memory, among other examples.

The central processing unit 206 may be configured to store, access, and execute computer-readable program instructions stored in the data storage 208 to perform the operations of an asset 200 described herein. For instance, as suggested above, the central processing unit 206 may be configured to receive respective sensor signals from the sensors 204 and/or actuators 205. The central processing unit 206 may be configured to store sensor and/or actuator 205 data in and later access it from the data storage 208. The central processing unit 206 may also be configured to determine whether received sensor signals trigger any abnormal-condition indicators, such as fault codes. For instance, the central processing unit 206 may be configured to store in the data storage 208 abnormal-condition rules, each of which include a given abnormal-condition indicator representing a particular abnormal condition and respective sensor criteria that trigger the abnormal-condition indicator. That is, each abnormal-condition indicator corresponds with one or more sensor measurement values that must be satisfied before the abnormal-condition indicator is triggered. In practice, the asset 200 may be pre-programmed with the abnormal-condition rules and/or may receive new abnormal-condition rules or updates to existing rules from a computing system, such as the analytics system 108.

In any event, the central processing unit 206 may be configured to determine whether received sensor signals trigger any abnormal-condition indicators. That is, the central processing unit 206 may determine whether received sensor signals satisfy any sensor criteria. When such a determination is affirmative, the central processing unit 206 may generate abnormal-condition data and may cause the asset's 200 network interface 210 to transmit the abnormal-condition data to the analytics system 108. The central processing unit 206 may generate abnormal-condition data and may also cause the asset's 200 user interface 212 to output an indication of the abnormal condition, such as a visual and/or audible alert. Additionally, the central processing unit 206 may log the occurrence of the abnormal-condition indicator being triggered in the data storage 208, perhaps with a timestamp.

Figure 3:
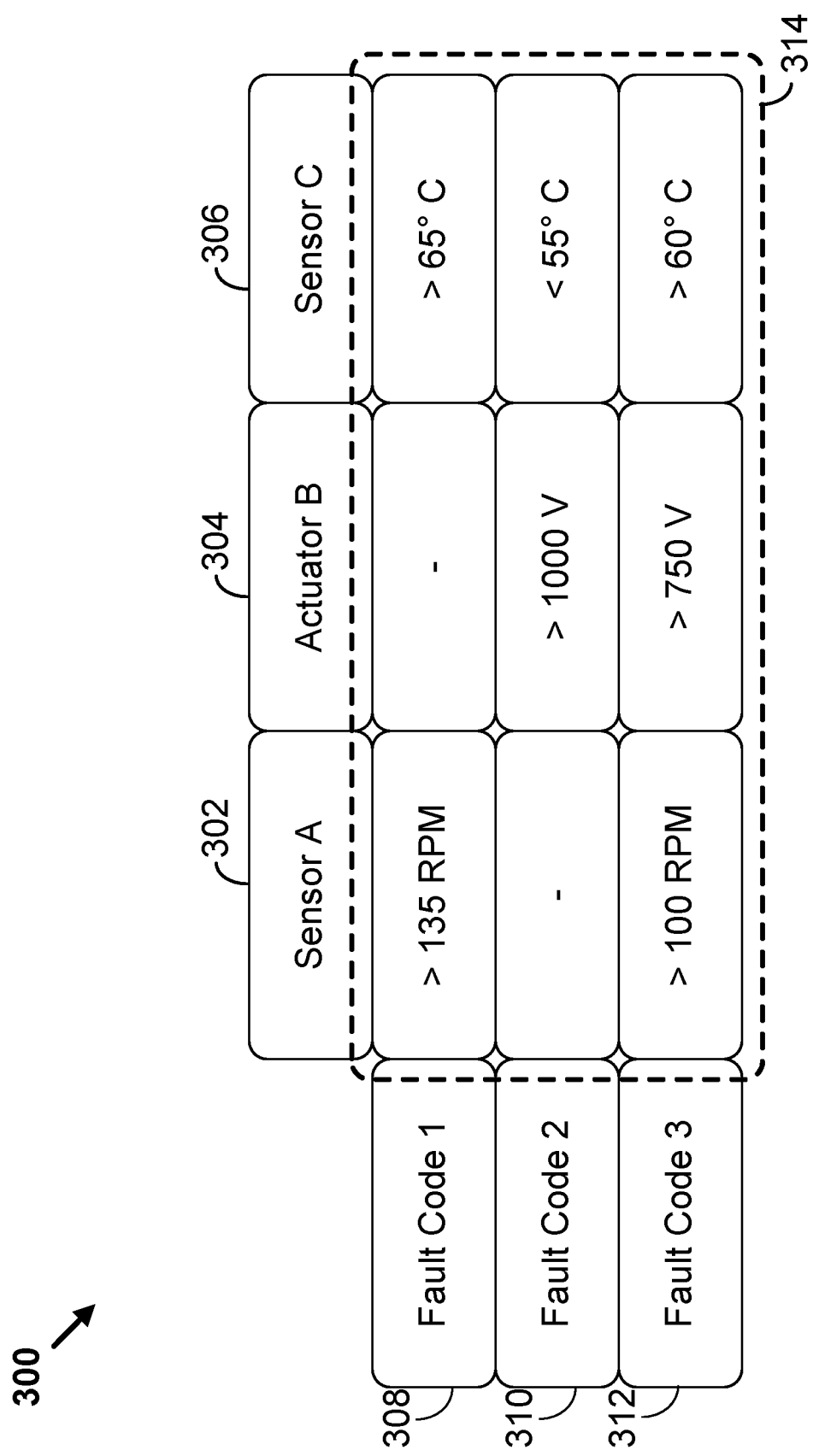
FIG. 3 depicts a conceptual illustration of example abnormal-condition indicators and triggering criteria.

FIG. 3 depicts a conceptual illustration of example abnormal-condition indicators and respective triggering criteria for an asset. In particular, FIG. 3 depicts a conceptual illustration of example fault codes. As shown, table 300 includes columns 302, 304, and 306 that correspond to Sensor A, Actuator B, and Sensor C, respectively, and rows 308, 310, and 312 that correspond to Fault Codes 1, 2, and 3, respectively. Entries 314 then specify sensor criteria (e.g., sensor value thresholds) that correspond to the given fault codes.

For example, Fault Code 1 will be triggered when Sensor A detects a rotational measurement greater than 135 revolutions per minute (RPM) and Sensor C detects a temperature measurement greater than 65° Celsius (C), Fault Code 2 will be triggered when Actuator B detects a voltage measurement greater than 1000 Volts (V) and Sensor C detects a temperature measurement less than 55° C., and Fault Code 3 will be triggered when Sensor A detects a rotational measurement greater than 100 RPM, Actuator B detects a voltage measurement greater than 750 V, and Sensor C detects a temperature measurement greater than 60° C. One of ordinary skill in the art will appreciate that FIG. 3 is provided for purposes of example and explanation only and that numerous other fault codes and/or triggering criteria are possible and contemplated herein.

Referring back to FIG. 2, the central processing unit 206 may be configured to carry out various additional functions for managing and/or controlling operations of the asset 200 as well. For example, the central processing unit 206 may be configured to provide instruction signals to the subsystems 202 and/or the sensors 204 that cause the subsystems 202 and/or the sensors 204 to perform some operation, such as modifying a throttle position or a sensor-sampling rate. Moreover, the central processing unit 206 may be configured to receive signals from the subsystems 202, the sensors 204, the network interfaces 210, and/or the user interfaces 212 and based on such signals, cause an operation to occur. Further still, the central processing unit 206 may be configured to receive signals from a computing device, such as a diagnostic device, that cause the central processing unit 206 to execute one or more diagnostic tools in accordance with diagnostic rules stored in the data storage 208. Other functionalities of the central processing unit 206 are discussed below.

In some implementations, the central processing unit 206 may be configured to receive a routing configuration or updates to the routing configuration from the analytics system 108 or another asset 200. The central processing unit 206 may cause the asset 200 to perform an operation based on the routing configuration or updates to the routing configuration.

The network interface 210 may be configured to provide for communication between the asset 200 and various other network components. For example, the network interface 210 may be configured to facilitate communications to and from the communication network 106 and may thus take the form of an antenna structure and associated equipment for transmitting and receiving various over-the-air signals and/or may take the form of a wired network interface. The network interface 210 may also be configured to provide for communication between the asset 200 and various network components operating in the mesh network 105. For example, the network interface 210 may be configured to facilitate communications between assets 102, 103, and 104 in the mesh network. Other examples are possible as well. In practice, the network interface 210 may be configured according to a communication protocol, such as any of those described above.

The user interface 212 may be configured to facilitate user interaction with the asset 200 and may also be configured to facilitate causing the asset 200 to perform an operation in response to user interaction. Examples of user interfaces 212 include touch-sensitive interfaces, mechanical interfaces (e.g., levers, buttons, wheels, dials, keyboards, etc.), and other input interfaces (e.g., microphones), among other examples. In some cases, the user interface 212 may include or provide connectivity to output components, such as display screens, speakers, headphone jacks, and the like.

The local analytics device 220 may generally be configured to receive and analyze data and based on such analysis, cause one or more operations to occur at the asset 200. In particular, the local analytics device 220 may receive sensor data from the sensors 204 and based on such data, may provide instructions to the central processing unit 206 that cause the asset 200 to perform an operation. For example, in some implementations, the local analytics device 220 may determine that the asset is likely to be unavailable, for example, based on a predictive model and data from the sensors 204. In response, the local analytics device 200 may generating a routing configuration for a mesh network (e.g., mesh network 105) and instruct the central processing unit 206 to transmit data based on the routing configuration. The local analytics device 200 may instruct the storage 208 to store the routing configuration and/or updates to the routing configuration.

In practice, the local analytics device 220 may enable the asset 200 to locally perform advanced analytics and associated operations, such as executing the predictive model, that may otherwise not be able to be performed with the other on-asset components. As such, the local analytics device 220 may help provide additional processing power and/or intelligence to the asset 200.

As shown, the local analytics device 220 may include a processing unit 222, a data storage 224, and a network interface 226, all of which may be communicatively linked by a system bus, network, or other connection mechanism. The processing unit 222 may include one or more processors, which may take any of the processor forms discussed above. In turn, the data storage 224 may be or include one or more non-transitory computer-readable storage media, which may take any of the forms of computer-readable storage media discussed above.

The processing unit 222 may be configured to store, access, and execute computer-readable program instructions stored in the data storage 224 to perform the operations of a local analytics device described herein. For instance, the processing unit 222 may be configured to receive respective sensor signals from the sensors 204 and execute a predictive model-workflow pair based on such signals. Other functions are described below.

The network interface 226 may be the same or similar to the network interfaces described above. In practice, the network interface 226 may facilitate communication between the asset 200 and the analytics system 108.

One of ordinary skill in the art will appreciate that the asset 200 shown in FIG. 2 is but one example of a simplified representation of an asset and that numerous others are also possible. For instance, other assets may include additional components not pictured and/or more or less of the pictured components.

III. Example Mesh Network

As mentioned above, the network configuration 100 may include a mesh network in which assets serve as nodes that cooperate to distribute data. In general, a mesh network includes a plurality of nodes that are configured to relay data from a source, perhaps that is located outside of the mesh network, through the mesh network to a destination in accordance with one or more routing protocols. The mesh network may be configured such that the nodes communicate with one another, as opposed to communicating directly with a central access point or the like, and may provide multiple possible paths by which data may travel from a source to a destination. Nodes may be dynamically added or removed helping to allow for a flexible communication network. Nodes may be mobile, in a fixed location, or some combination thereof.

Figure 4:
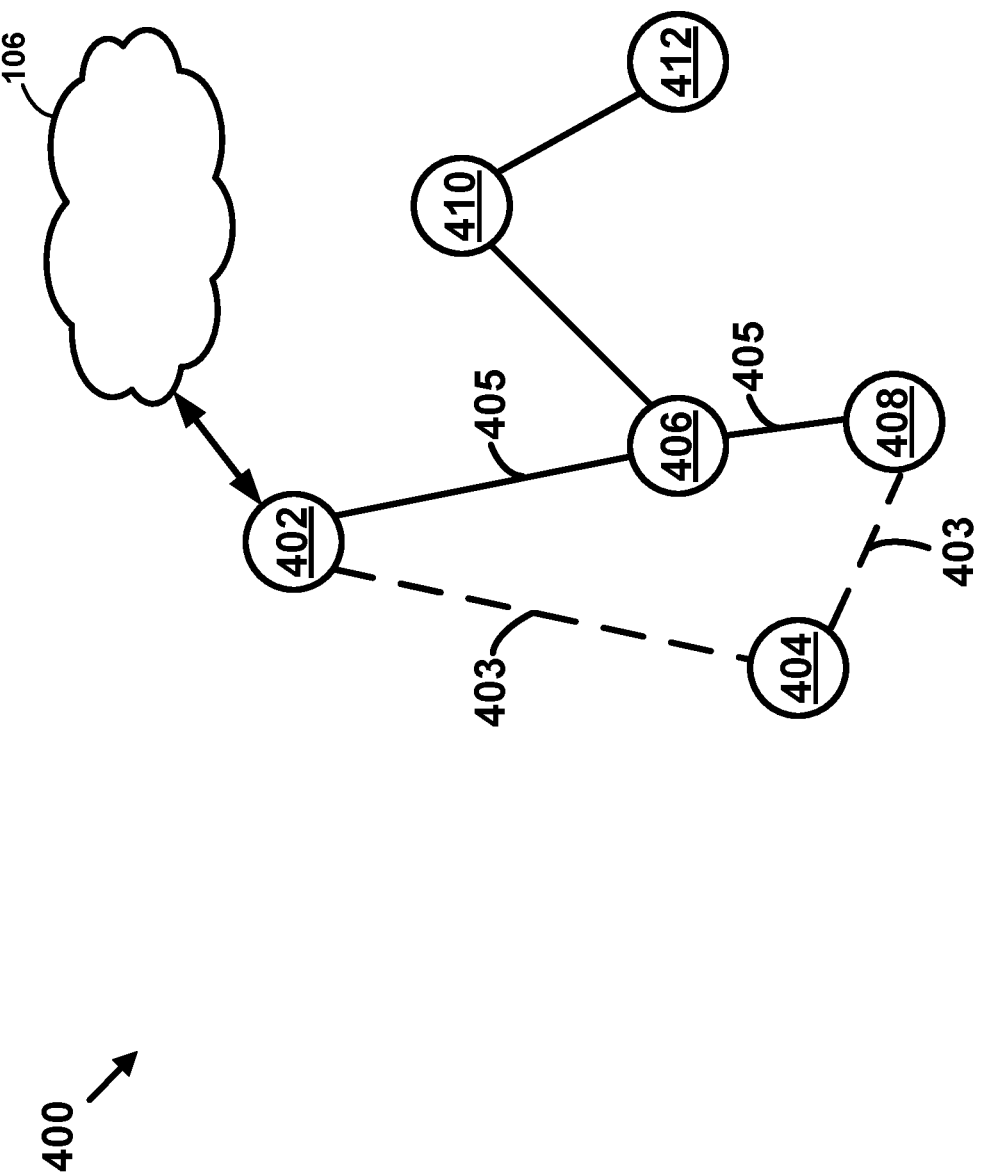
FIG. 4 depicts a conceptual illustration of a mesh network.

FIG. 4 depicts a conceptual illustration of an example mesh network 400 that is communicatively coupled to another communication network (e.g., the communication network 106). As shown, the mesh network 400 includes a plurality of nodes 402, 404, 406, 408, 410, and 412. In this example, the nodes 404 and 406 are directly reachable by the node 402, while the nodes 408, 410, and 412 are not directly reachable by the node 402. As such, the mesh network 400 may be advantageous in that the nodes 404 and 406 extend the transmission range of the node 402, among other advantages.

In example implementations, the node 402 may be configured to provide the mesh network 400 connectivity to the communication network 106 (e.g., and thus WANs). In this way, the node 402 allows the other nodes of the mesh network 400 to share a single connection back to the communication network 106. The node 402 may be communicatively coupled to the communication network 106 via a wired or wireless mechanism or some combination thereof. The node 402 may include, take the form of, or otherwise communicate with an access point, such as a wireless router or the like. In some implementations, the node 402 may take the form of an asset, such as the asset 200.

The nodes 404-412 may take the form of assets, some of which may be all of the same type and/or class or may differ in some respects. In any event, each of the assets 404-412 serving as nodes may be configured to route data in accordance with one or more routing techniques. For example, each asset may include one or more network interfaces that allow the asset to receive and transmit data, such as any of network interfaces discussed above with reference to FIG. 2. In some implementations, a given asset may be a "legacy" asset that does not itself include a communications interface but may be retrofitted with an external network interface that provides the given asset connectivity to the mesh network 400. Moreover, in example implementations, an asset may be configured to receive but not transmit data. For example, the asset 412 may be a data storage device that receives and stores data but does not transmit data to other nodes in the mesh network 400. Other examples are also possible.

As suggested above, data may propagate through the mesh network 400 in accordance with one or more routing techniques. Generally, a given routing technique may provide multiple paths by which data from a source can reach a destination via intermediary nodes (i.e., nodes that are not the final destination for the data). And when the data is sent, the path that provides the quickest and/or most reliable route may be utilized. As an example, a given routing technique may provide two paths between the communication network 106 and the asset 408 (e.g., path 403 and path 405). As such, data that originates from the asset 408 (e.g., operating data) may travel to the communication network 106 via the path 403 (e.g., passing through intermediary nodes 404 and 402), while data that originates from the communication network 106 may travel to the asset 408 via the path 405 (e.g., passing through intermediary nodes 402 and 406), among other possibilities.

Various routing techniques may be utilized, such as reactive routing techniques (e.g., ad-hoc on demand distance vector routing (AODV), dynamic source routing (DSR), etc.), proactive routing techniques (e.g., optimized link state routing (OLSR), better approach to mobile ad-hoc networking (BATMAN), destination sequenced distance-vector routing (DSDV), cluster head gateway switch routing (CGSR), etc.), and/or hybrid routing techniques (e.g., some combination of reactive and proactive routing techniques), among other routing techniques.

Depending on the given routing technique, the paths by which data may propagate through the mesh network 400 may be determined in a variety of manners. Generally, the paths are determined by each node of the mesh network 400 exchanging, perhaps periodically, respective routing information (e.g., distance vectors, node metrics, etc.) with the other nodes to establish the possible routes from each node to the other in the mesh network 400. More specifically, the mesh network 400 may be established and paths may be determined based on the routing information of the nodes 402-412. The routing information of a given node may include or be based on various node metrics, such as a current load on the given node, radio frequency noise level, GPS coordinates of the given node, received signal strength indicator, signal-to-noise ratio, compass angle, remaining battery power of the given node, and/or remaining energy of the given node (e.g., an indication of the given node's data throughput and/or a number of hops), among other considerations.

Each node may then store some or all of the routing information of the other nodes, such as in the form of a routing table, in accordance with a given routing technique. Generally, a given routing technique may cause the nodes to determine one or more "optimal" paths to distribute data based on the routing information. For instance, the nodes may optimize for the quickest data delivery (e.g., fewest number of hops, shortest overall distance, and/or shortest travel time), the most reliable data delivery, or the path that optimizes both quickness and reliability, among other examples. In any event, the nodes may configure their respective routing tables to reflect the optimized data delivery such that, when a given node receives data that is destined for a particular node, the given node can readily determine the node to which it should relay the data (e.g., the "next hop") to facilitate delivering the data in accordance with the given routing technique.

In practice, the mesh network 400 may be dynamically updated as network conditions and/or node metrics change. For example, as network conditions change (e.g., as network latency increases or decreases), the nodes may determine that a given path is less optimal than another path and update their respective routing tables to reflect that a different path is now the most optimal path. In another example, as a given node's ability to server as router changes (e.g., as the given asset's health decreases, discussed in further detail below), the nodes may determine that a given path (e.g., one in which the given node is a link in the path) is less optimal than another path and update their respective route tables accordingly. Other examples of updating routing information are also possible.

IV. Example Analytics System

Figure 5:
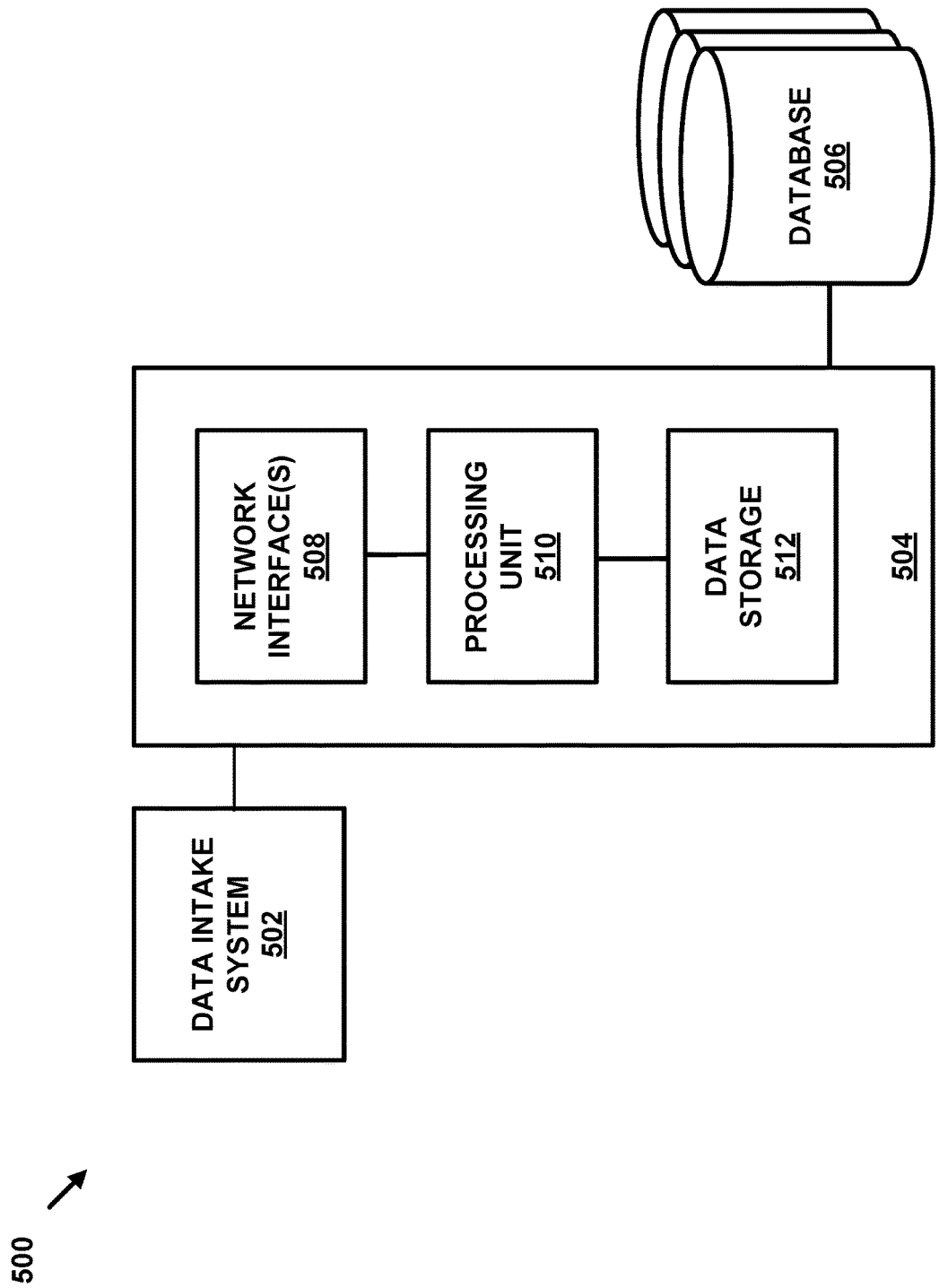
FIG. 5 depicts a simplified block diagram of an example analytics system.

Referring now to FIG. 5, a simplified block diagram of an example analytics system 500 is depicted. As suggested above, the analytics system 500 may include one or more computing systems communicatively linked and arranged to carry out various operations described herein. Specifically, as shown, the analytics system 500 may include a data intake system 502, a data science system 504, and one or more databases 506. These system components may be communicatively coupled via one or more wireless and/or wired connections.

The data intake system 502 may generally function to receive and process data and output data to the data science system 504. As such, the data intake system 502 may include one or more network interfaces configured to receive data from various network components of the network configuration 100, such as the assets 102, 103, and 104, the output system 110, and/or the data source 112. Specifically, the data intake system 502 may be configured to receive analog signals, data streams, and/or network packets, among other examples. As such, the network interfaces may include one or more wired network interfaces, such as a port or the like, and/or wireless network interfaces, similar to those described above. In some examples, the data intake system 402 may be or include components configured according to a given dataflow technology, such as a NiFi receiver or the like.

The data intake system 502 may include one or more processing components configured to perform one or more operations. Example operations may include compression and/or decompression, encryption and/or de-encryption, analog-to-digital and/or digital-to-analog conversion, filtration, and amplification, among other operations. Moreover, the data intake system 502 may be configured to parse, sort, organize, and/or route data based on data type and/or characteristics of the data. In some examples, the data intake system 502 may be configured to format, package, and/or route data based on one or more characteristics or operating parameters of the data science system 504.

In general, the data received by the data intake system 502 may take various forms. For example, the payload of the data may include a single sensor measurement, multiple sensor measurements and/or one or more fault codes. Other examples are also possible.

Moreover, the received data may include certain characteristics, such as a source identifier and a timestamp (e.g., a date and/or time at which the information was obtained). For instance, a unique identifier (e.g., a computer generated alphabetic, numeric, alphanumeric, or the like identifier) may be assigned to each asset, and perhaps to each sensor. Such identifiers may be operable to identify the asset, or sensor, from which data originates. In some cases, another characteristic may include the location (e.g., GPS coordinates) at which the information was obtained. Data characteristics may come in the form of signal signatures or metadata, among other examples.

The data science system 504 may generally function to receive (e.g., from the data intake system 502) and analyze data and based on such analysis, cause one or more operations to occur. As such, the data science system 504 may include one or more network interfaces 508, a processing unit 510, and data storage 512, all of which may be communicatively linked by a system bus, network, or other connection mechanism. In some cases, the data science system 404 may be configured to store and/or access one or more application program interfaces (APIs) that facilitate carrying out some of the functionality disclosed herein.

The network interfaces 508 may be the same or similar to any network interface described above. In practice, the network interfaces 508 may facilitate communication between the data science system 504 and various other entities, such as the data intake system 502, the databases 506, the assets 102, 103, 104, the output system 110, etc.

The processing unit 510 may include one or more processors, which may take any of the processor forms described above. In turn, the data storage 512 may be or include one or more non-transitory computer-readable storage media, which may take any of the forms of computer-readable storage media discussed above. The processing unit 510 may be configured to store, access, and execute computer-readable program instructions stored in the data storage 512 to perform the operations of an analytics system described herein.

In general, the processing unit 510 may be configured to perform analytics on data received from the data intake system 502. To that end, the processing unit 510 may be configured to execute one or more modules, which may each take the form of one or more sets of program instructions that are stored in the data storage 512. The modules may be configured to facilitate causing an outcome to occur based on the execution of the respective program instructions. An example outcome from a given module may include outputting data into another module, updating the program instructions of the given module and/or of another module, and outputting data to a network interface 508 for transmission to an asset and/or the output system 110, among other examples.

The databases 506 may generally function to receive (e.g., from the data science system 504) and store data. As such, each database 506 may include one or more non-transitory computer-readable storage media, such as any of the examples provided above. In practice, the databases 506 may be separate from or integrated with the data storage 512.

The databases 506 may be configured to store numerous types of data, some of which is discussed below. In practice, some of the data stored in the databases 506 may include a timestamp indicating a date and time at which the data was generated or added to the database. Moreover, data may be stored in a number of manners in the databases 506. For instance, data may be stored in time sequence, in a tabular manner, and/or organized based on data source type (e.g., based on asset, asset type, sensor, or sensor type) or fault code, among other examples.

V. Example Operations

The operations of the example network configuration 100 depicted in FIG. 1 will now be discussed in further detail below. To help describe some of these operations, flow diagrams may be referenced to describe combinations of operations that may be performed. In some cases, each block may represent a module or portion of program code that includes instructions that are executable by a processor to implement specific logical functions or steps in a process. The program code may be stored on any type of computer-readable medium, such as non-transitory computer-readable media. In other cases, each block may represent circuitry that is wired to perform specific logical functions or steps in a process. Moreover, the blocks shown in the flow diagrams may be rearranged into different orders, combined into fewer blocks, separated into additional blocks, and/or removed based upon the particular embodiment.

The following description may reference examples where a single data source, such as an asset 102, provides data to the analytics system 108 that then performs one or more functions. It should be understood that this is done merely for sake of clarity and explanation and is not meant to be limiting. In practice, the analytics system 108 may receive data from multiple sources, such as assets 102, 103, and 104, perhaps simultaneously, and perform operations based on such aggregate received data.

A. Generating Routing Topologies

In example implementations, some or all of the assets 102, 103, and 104 may exchange setup messages to establish the mesh network 105 over which the assets and the analytics system 108 may transfer data. Specifically, the mesh network 105 may be established between the assets 102-104 in line with the above discussion with reference to FIG. 4.

In some implementations, the assets 102-104 may generate routing topologies (e.g., routing tables that reflect paths to transfer data) to facilitate optimizing the mesh network 105 according to desired optimization factors. For example, the routing topologies may indicate paths that are optimized for fewest number of assets (nodes) that relay data (e.g., hop minimization), shortest data delivery time (e.g., latency minimization), lowest energy expenditure (e.g., energy minimization), least amount of redundancy, some combination thereof, or any of the other examples provided above, among other examples. In example implementations, the assets 102-104 may exchange routing information with one another and/or the analytics system 108. As network conditions and/or asset (node) metrics change, the routing topologies may be updated in accordance with the desired optimization factors.

B. Collecting Operating Data

As mentioned above, the representative asset 102 may take various forms and may be configured to perform a number of operations. In a non-limiting example, the asset 102 may take the form of a locomotive that is operable to transfer cargo across the United States. While in transit, the sensors of the asset 102 may obtain sensor data that reflects one or more operating conditions of the asset 102. The sensors may transmit the sensor data to a processing unit of the asset 102.

The processing unit may be configured to receive sensor data from the sensors. In practice, the processing unit may receive sensor data from multiple sensors simultaneously or sequentially. As discussed above, while receiving the sensor data, the processing unit may also be configured to determine whether sensor data satisfies sensor criteria that trigger any abnormal-condition indicators, such as fault codes. In the event the processing unit determines that one or more abnormal-condition indicators are triggered, the processing unit may be configured to perform one or more local operations, such as outputting an indication of the triggered indicator via a user interface.

The asset 102 may then transmit operating data to the analytics system 108 via a network interface of the asset 102 and the communication network 106. In operation, the asset 102 may transmit operating data to the analytics system 108 continuously, periodically, and/or in response to triggering events (e.g., abnormal conditions). Specifically, the asset 102 may transmit operating data periodically based on a particular frequency (e.g., daily, hourly, every fifteen minutes, once per minute, once per second, etc.), or the asset 102 may be configured to transmit a continuous, real-time feed of operating data. Additionally or alternatively, the asset 102 may be configured to transmit operating data based on certain triggers, such as when sensor measurements from its sensors satisfy sensor criteria for any abnormal-condition indicators. The asset 102 may transmit operating data in other manners as well.

In practice, operating data for the asset 102 may include sensor data and/or abnormal-condition data. In some implementations, the asset 102 may be configured to provide the operating data in a single data stream, while in other implementations the asset 102 may be configured to provide the operating data in multiple, distinct data streams. For example, the asset 102 may provide to the analytics system 108 a first data stream of sensor data and a second data stream of abnormal-condition data. Other possibilities also exist.

Sensor data may take various forms. For example, at times, sensor data may include measurements obtained by each of the sensors of the asset 102. While at other times, sensor data may include measurements obtained by a subset of the sensors of the asset 102.

Specifically, the sensor data may include measurements obtained by the sensors associated with a given triggered abnormal-condition indicator. For example, if a triggered fault code is Fault Code 1 from FIG. 3, then the sensor data may include raw measurements obtained by Sensors A and C. Additionally or alternatively, the sensor data may include measurements obtained by one or more sensors not directly associated with the triggered fault code. Continuing off the last example, the sensor data may additionally include measurements obtained by Sensor B and/or other sensors. In some examples, the asset 102 may include particular sensor data in the operating data based on a fault-code rule or instruction provided by the analytics system 108, which may have, for example, determined that there is a correlation between that which Sensor B is measuring and that which caused the Fault Code 1 to be triggered in the first place. Other examples are also possible.

Further still, the sensor data may include one or more sensor measurements from each sensor of interest based on a particular time of interest, which may be selected based on a number of factors. In some examples, the particular time of interest may be based on a sampling rate. In other examples, the particular time of interest may be based on the time at which an abnormal-condition indicator is triggered.

In particular, based on the time at which an abnormal-condition indicator is triggered, the sensor data may include one or more respective sensor measurements from each sensor of interest (e.g., sensors directly and indirectly associated with the triggered indicator). The one or more sensor measurements may be based on a particular number of measurements or particular duration of time around the time of the triggered abnormal-condition indicator.

For example, if a triggered fault code is Fault Code 2 from FIG. 3, the sensors of interest might include Sensors B and C. The one or more sensor measurements may include the most recent respective measurements obtained by Sensors B and C prior to the triggering of the fault code (e.g., triggering measurements) or a respective set of measurements before, after, or about the triggering measurements. For example, a set of five measurements may include the five measurements before or after the triggering measurement (e.g., excluding the triggering measurement), the four measurements before or after the triggering measurement and the triggering measurement, or the two measurements before and the two after as well as the triggering measurement, among other possibilities.

Similar to sensor data, the abnormal-condition data may take various forms. In general, the abnormal-condition data may include or take the form of an indicator that is operable to uniquely identify a particular abnormal condition that occurred at the asset 102 from all other abnormal conditions that may occur at the asset 102. The abnormal-condition indicator may take the form of an alphabetic, numeric, or alphanumeric identifier, among other examples. Moreover, the abnormal-condition indicator may take the form of a string of words that is descriptive of the abnormal condition, such as "Overheated Engine" or "Out of Fuel", among other examples.

The analytics system 108, and in particular, the data intake system of the analytics system 108, may be configured to receive operating data from one or more assets and/or data sources. The data intake system may be configured to perform one or more operations to the received data and then relay the data to the data science system of the analytics system 108. In turn, the data science system may analyze the received data and based on such analysis, perform one or more operations.

C. Defining Predictive Models & Workflows

As one example, the analytics system 108 may be configured to define predictive models and corresponding workflows based on received operating data for one or more assets and/or received external data related to the one or more assets. The analytics system 108 may define model-workflow pairs based on various other data as well.

In general, a model-workflow pair may include a set of program instructions that cause an asset to monitor certain operating conditions and carry out certain operations that help facilitate preventing the occurrence of a particular event suggested by the monitored operating conditions. Specifically, a predictive model may include one or more algorithms whose inputs are sensor data from one or more sensors of an asset and whose outputs are utilized to determine a probability that a particular event may occur at the asset within a particular period of time in the future. In turn, a workflow may include one or more triggers (e.g., model output values) and corresponding operations that the asset carries out based on the triggers.

As suggested above, the analytics system 108 may be configured to define aggregate and/or individualized predictive models and/or workflows. An "aggregate" model/workflow may refer to a model/workflow that is generic for a group of assets and defined without taking into consideration particular characteristics of the assets to which the model/workflow is deployed. On the other hand, an "individualized" model/workflow may refer to a model/workflow that is specifically tailored for a single asset or a subgroup of assets from the group of assets and defined based on particular characteristics of the single asset or subgroup of assets to which the model/workflow is deployed.

According to the present disclosure, one implementation of a model-workflow pair may take the form of a model for predicting that a given asset is likely to be unavailable within a given period of time in the future and a corresponding workflow for causing a routing table to be updated based on this predictive model. This model-workflow pair may take various forms.

1. Predictive Model for Asset Unavailability

As noted above, the analytics system 108 may be configured to define a model for predicting that a given asset is likely to be unavailable within a given period of time in the future (i.e., an "unavailability model"). The analytics system 108 may carry out this step in various manners.

Figure 6:
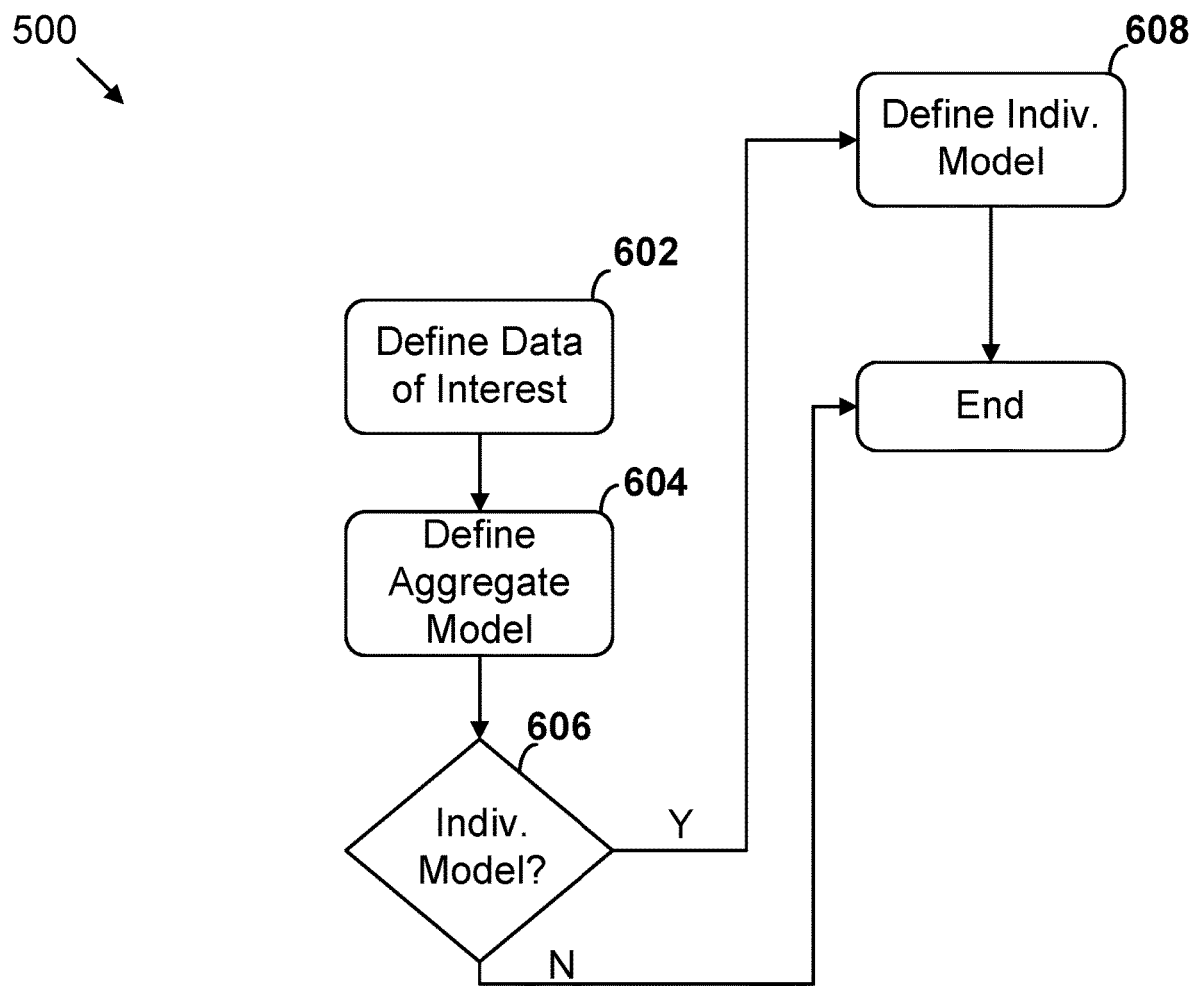
FIG. 6 depicts an example flow diagram of a definition phase that may be used for defining model-workflow pairs.

FIG. 6 is a flow diagram 600 depicting one possible example of a definition phase that may be used for defining the unavailability model. For purposes of illustration, the example definition phase is described as being carried out by the analytics system 108, but this definition phase may be carried out by other systems as well. One of ordinary skill in the art will appreciate that the flow diagram 600 is provided for sake of clarity and explanation and that numerous other combinations of operations may be utilized to define a model-workflow pair.

As shown in FIG. 6, at block 602, the analytics system 108 may begin by defining a set of data that forms the basis for a given unavailability model (e.g., the data of interest). The data of interest may derive from a number of sources, such as the assets 102, 103, and 104 and the data source 112, and may be stored in a database of the analytics system 108.

The data of interest may include historical data for a particular set of assets from a group of assets or all of the assets from a group of assets (e.g., the assets of interest). Moreover, the data of interest may include measurements from a particular set of sensors and/or actuators from each of the assets of interest or from all of the sensors and/or actuators from each of the assets of interest. Further still, the data of interest may include data from a particular period of time in the past, such as two weeks' worth of historical data.

The data of interest may include a variety of types data, which may depend on the given unavailability model. In some instances, the data of interest may include at least operating data indicating operating conditions of assets, where the operating data is as discussed above in the Collection of Operating Data section. Additionally, the data of interest may include environment data indicating environments in which assets are typically operated and/or scheduling data indicating planned dates and times during which assets are to carry out certain tasks. Other types of data may also be included in the data of interest.

In practice, the data of interest may be defined in a number of manners. In one example, the data of interest may be user-defined. In particular, a user may operate an output system 110 that receives user inputs indicating a selection of certain data of interest, and the output system 110 may provide to the analytics system 108 data indicating such selections. Based on the received data, the analytics system 108 may then define the data of interest.

In another example, the data of interest may be machine-defined. In particular, the analytics system 108 may perform various operations, such as simulations, to determine the data of interest that generates the most accurate predictive model. Other examples are also possible.

Returning to FIG. 6, at block 604, the analytics system 108 may be configured to, based on the data of interest, define an aggregate, predictive model that represents a relationship between operating conditions of an asset and a likelihood of the asset becoming unavailable within a given period of time in the future. Specifically, an aggregate, predictive model may receive as inputs sensor data from sensors of an asset and/or actuator data from actuators of the asset and may output a probability that the asset will become unavailable within a given period of time in the future.

In general, defining the aggregate, predictive model may involve utilizing one or more modeling techniques to generate a model that returns a probability between zero and one, such as a random forest technique, logistic regression technique, or other regression technique, among other modeling techniques. However, other techniques are possible as well.

In one particular example implementation, the unavailability model may take the form of a predictive model that monitors the health of an asset and outputs a health metric (e.g., "health score") for an asset, which is a single, aggregated metric that indicates whether a failure will occur at a given asset (and thus whether the given asset will become unavailable) within a given timeframe into the future. In particular, a health metric may indicate a likelihood that no failures from a group of failures will occur at an asset within a given timeframe into the future, or a health metric may indicate a likelihood that at least one failure from a group of failures will occur at an asset within a given timeframe into the future.

Depending on the desired granularity of the health metric, the analytics system 108 may be configured to define different predictive models that output different levels of health metrics, each of which may be used as the unavailability model. For example, the analytics system 108 may define a predictive model that outputs a health metric for the asset as a whole (i.e., an asset-level health metric). As another example, the analytics system 108 may define a respective predictive model that outputs a respective health metric for one or more subsystems of the asset (i.e., subsystem-level health metrics). In some cases, the outputs of each subsystem-level predictive model may be combined to generate an asset-level health metric. Other examples are also possible.

Figure 7:
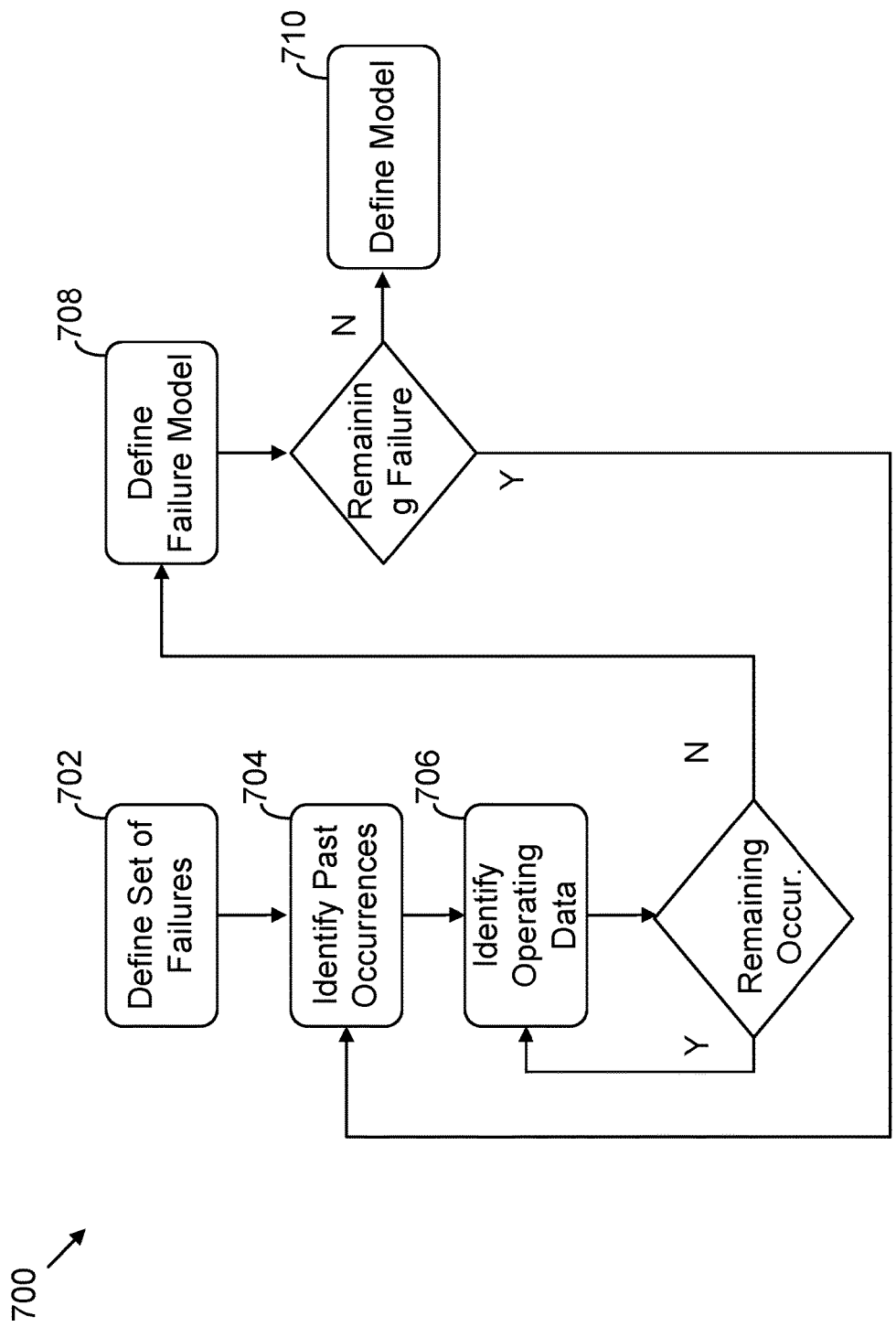
FIG. 7 depicts an example flow diagram of a modeling phase that may be used for defining a predictive model that outputs a health metric.

In general, defining a predictive model that outputs a health metric may be performed in a variety of manners. FIG. 7 is a flow diagram 700 depicting one possible example of a modeling phase that may be used for defining a model that outputs a health metric. For purposes of illustration, the example modeling phase is described as being carried out by the analytics system 108, but this modeling phase may be carried out by other systems as well. One of ordinary skill in the art will appreciate that the flow diagram 700 is provided for sake of clarity and explanation and that numerous other combinations of operations may be utilized to determine a health metric.

As shown in FIG. 7, at block 702, the analytics system 108 may begin by defining a set of the one or more failures that form the basis for the health metric (i.e., the failures of interest). In practice, the one or more failures may be those failures that could render an asset (or a subsystem thereof) inoperable if they were to occur. Based on the defined set of failures, the analytics system 108 may take steps to define a model for predicting a likelihood of any of the failures occurring within a given timeframe in the future (e.g., the next two weeks).

In particular, at block 704, the analytics system 108 may analyze historical operating data for a group of one or more assets to identify past occurrences of a given failure from the set of failures. At block 706, the analytics system 108 may identify a respective set of operating data that is associated with each identified past occurrence of the given failure (e.g., sensor and/or actuator data from a given timeframe prior to the occurrence of the given failure). At block 708, the analytics system 108 may analyze the identified sets of operating data associated with past occurrences of the given failure to define a relationship (e.g., a failure model) between (1) the values for a given set of operating metrics and (2) the likelihood of the given failure occurring within a given timeframe in the future (e.g., the next two weeks). Lastly, at block 710, the defined relationship for each failure in the defined set (e.g., the individual failure models) may then be combined into a model for predicting the overall likelihood of a failure occurring.

As the analytics system 108 continues to receive updated operating data for the group of one or more assets, the analytics system 108 may also continue to refine the predictive model for the defined set of one or more failures by repeating steps 704-710 on the updated operating data.

The functions of the example modeling phase illustrated in FIG. 7 will now be described in further detail. Starting with block 702, as noted above, the analytics system 108 may begin by defining a set of the one or more failures that form the basis for the health metric. The analytics system 108 may perform this function in various manners.

In one example, the set of the one or more failures may be based on one or more user inputs. Specifically, the analytics system 108 may receive from a computing system operated by a user, such as the output system 110, input data indicating a user selection of the one or more failures. As such, the set of one or more failures may be user-defined.

In other examples, the set of the one or more failures may be based on a determination made by the analytics system 108 (e.g., machine-defined). In particular, the analytics system 108 may be configured to define the set of one or more failures, which may occur in a number of manners.

For instance, the analytics system 108 may be configured to define the set of failures based on one or more characteristics of the asset 102. That is, certain failures may correspond to certain characteristics, such as asset type, class, etc., of an asset. For example, each type and/or class of asset may have respective failures of interest.

In another instance, the analytics system 108 may be configured to define the set of failures based on historical data stored in the databases of the analytics system 108 and/or external data provided by the data source 112. For example, the analytics system 108 may utilize such data to determine which failures result in the longest repair-time and/or which failures are historically followed by additional failures, among other examples.

In yet other examples, the set of one or more failures may be defined based on a combination of user inputs and determinations made by the analytics system 108. Other examples are also possible.

At block 704, for each of the failures from the set of failures, the analytics system 108 may analyze historical operating data for a group of one or more assets (e.g., abnormal-behavior data) to identify past occurrences of a given failure. The group of the one or more assets may include a single asset, such as asset 102, or multiple assets of a same or similar type, such as fleet of assets that includes the assets 102, 103, and 104. The analytics system 108 may analyze a particular amount of historical operating data, such as a certain amount of time's worth of data (e.g., a month's worth) or a certain number of data-points (e.g., the most recent thousand data-points), among other examples.

In practice, identifying past occurrences of the given failure may involve the analytics system 108 identifying the type of operating data, such as abnormal-condition data, that indicates the given failure. In general, a given failure may be associated with one or multiple abnormal-condition indicators, such as fault codes. That is, when the given failure occurs, one or multiple abnormal-condition indicators may be triggered. As such, abnormal-condition indicators may be reflective of an underlying symptom of a given failure.

After identifying the type of operating data that indicates the given failure, the analytics system 108 may identify the past occurrences of the given failure in a number of manners. For instance, the analytics system 108 may locate, from historical operating data stored in the databases of the analytics system 108, abnormal-condition data corresponding to the abnormal-condition indicators associated with the given failure. Each located abnormal-condition data would indicate an occurrence of the given failure. Based on this located abnormal-condition data, the analytics system 108 may identify a time at which a past failure occurred.

At block 706, the analytics system 108 may identify a respective set of operating data that is associated with each identified past occurrence of the given failure. In particular, the analytics system 108 may identify a set of sensor and/or actuator data from a certain timeframe around the time of the given occurrence of the given failure. For example, the set of data may be from a particular timeframe (e.g., two weeks) before, after, or around the given occurrence of the failure. In other cases, the set of data may be identified from a certain number of data-points before, after, or around the given occurrence of the failure.

In example implementations, the set of operating data may include sensor and/or actuator data from some or all of the sensors and actuators of the asset 102. For example, the set of operating data may include data from sensors and/or actuators associated with an abnormal-condition indicator corresponding to the given failure.

Returning to FIG. 7, after the analytics system 108 identifies the set of operating data for the given occurrence of the given failure, the analytics system 108 may determine whether there are any remaining occurrences for which a set of operating data should be identified. In the event that there is a remaining occurrence, block 706 would be repeated for each remaining occurrence.

Thereafter, at block 708, the analytics system 108 may analyze the identified sets of operating data associated with the past occurrences of the given failure to define a relationship (e.g., a failure model) between (1) a given set of operating metrics (e.g., a given set of sensor and/or actuator measurements) and (2) the likelihood of the given failure occurring within a given timeframe in the future (e.g., the next two weeks). That is, a given failure model may take as inputs sensor and/or actuator measurements from one or more sensors and/or actuators and output a probability that the given failure will occur within the given timeframe in the future.

In general, a failure model may define a relationship between operating conditions of the asset 102 and the likelihood of a failure occurring. In some implementations, in addition to raw data signals from sensors and/or actuators of the asset 102, a failure model may receive a number of other data inputs, also known as features, which are derived from the sensor and/or actuator signals. Such features may include an average or range of values that were historically measured when a failure occurred, an average or range of value gradients (e.g., a rate of change in measurements) that were historically measured prior to an occurrence of a failure, a duration of time between failures (e.g., an amount of time or number of data-points between a first occurrence of a failure and a second occurrence of a failure), and/or one or more failure patterns indicating sensor and/or actuator measurement trends around the occurrence of a failure. One of ordinary skill in the art will appreciate that these are but a few example features that can be derived from sensor and/or actuator signals and that numerous other features are possible.

In practice, a failure model may be defined in a number of manners. In example implementations, the analytics system 108 may define a failure model by utilizing one or more modeling techniques that return a probability between zero and one, which may take the form of any modeling techniques described above.

In a particular example, defining a failure model may involve the analytics system 108 generating a response variable based on the historical operating data identified at block 706. Specifically, the analytics system 108 may determine an associated response variable for each set of sensor and/or actuator measurements received at a particular point in time. As such, the response variable may take the form of a data set associated with the failure model.

The response variable may indicate whether the given set of measurements is within any of the timeframes determined at block 706. That is, a response variable may reflect whether a given set of data is from a time of interest about the occurrence of a failure. The response variable may be a binary-valued response variable such that, if the given set of measurements is within any of determined timeframes, the associated response variable is assigned a value of one, and otherwise, the associated response variable is assigned a value of zero.

Continuing in the particular example of defining a failure model based on a response variable, the analytics system 108 may train the failure model with the historical operating data identified at block 706 and the generated response variable. Based on this training process, the analytics system 108 may then define the failure model that receives as inputs various sensor and/or actuator data and outputs a probability between zero and one that a failure will occur within a period of time equivalent to the timeframe used to generate the response variable.

In some cases, training with the historical operating data identified at block 706 and the generated response variable may result in variable importance statistics for each sensor and/or actuator. A given variable importance statistic may indicate the sensor's or actuator's relative effect on the probability that a given failure will occur within the period of time into the future.

Additionally or alternatively, the analytics system 108 may be configured to define a failure model based on one or more survival analysis techniques, such as a Cox proportional hazard technique. The analytics system 108 may utilize a survival analysis technique in a manner similar in some respects to the above-discussed modeling technique, but the analytics system 108 may determine a survival time-response variable that indicates an amount of time from the last failure to a next expected event. A next expected event may be either reception of senor and/or actuator measurements or an occurrence of a failure, whichever occurs first. This response variable may include a pair of values that are associated with each of the particular points in time at which measurements are received. The response variable may then be utilized to determine a probability that a failure will occur within the given timeframe in the future.

In some example implementations, the failure model may be defined based in part on external data, such as weather data, and "hotbox" data, among other data. For instance, based on such data, the failure model may increase or decrease an output failure probability.

In practice, external data may be observed at points in time that do not coincide with times at which asset sensors and/or actuators obtain measurements. For example, the times at which "hotbox" data is collected (e.g., times at which a locomotive passes along a section of railroad track that is outfitted with hot box sensors) may be in disagreement with sensor and/or actuator measurement times. In such cases, the analytics system 108 may be configured to perform one or more operations to determine external data observations that would have been observed at times that correspond to the sensor measurement times.

Specifically, the analytics system 108 may utilize the times of the external data observations and times of the measurements to interpolate the external data observations to produce external data values for times corresponding to the measurement times. Interpolation of the external data may allow external data observations or features derived therefrom to be included as inputs into the failure model. In practice, various techniques may be used to interpolate the external data with the sensor and/or actuator data, such as nearest-neighbor interpolation, linear interpolation, polynomial interpolation, and spline interpolation, among other examples.

Returning to FIG. 7, after the analytics system 108 determines a failure model for a given failure from the set of failures defined at block 702, the analytics system 108 may determine whether there are any remaining failures for which a failure model should be determined. In the event that there remains a failure for which a failure model should be determined, the analytics system 108 may repeat the loop of blocks 704-708. In some implementations, the analytics system 108 may determine a single failure model that encompasses all of the failures defined at block 702. In other implementations, the analytics system 108 may determine a failure model for each subsystem of the asset 102, which may then be utilized to determine an asset-level failure model. Other examples are also possible.

Lastly, at block 710, the defined relationship for each failure in the defined set (e.g., the individual failure models) may then be combined into the model (e.g., the health-metric model) for predicting the overall likelihood of a failure occurring within the given timeframe in the future (e.g., the next two weeks). That is, the model receives as inputs sensor and/or actuator measurements from one or more sensors and/or actuators and outputs a single probability that at least one failure from the set of failures will occur within the given timeframe in the future.

The analytics system 108 may define the health-metric model in a number of manners, which may depend on the desired granularity of the health metric. That is, in instances where there are multiple failure models, the outcomes of the failure models may be utilized in a number of manners to obtain the output of the health-metric model. For example, the analytics system 108 may determine a maximum, median, or average from the multiple failure models and utilize that determined value as the output of the health-metric model.

In other examples, determining the health-metric model may involve the analytics system 108 attributing a weight to individual probabilities output by the individual failure models. For instance, each failure from the set of failures may be considered equally undesirable, and so each probability may likewise be weighted the same in determining the health-metric model. In other instances, some failures may be considered more undesirable than others (e.g., more catastrophic or require longer repair time, etc.), and so those corresponding probabilities may be weighted more than others.

In yet other examples, determining the health-metric model may involve the analytics system 108 utilizing one or more modeling techniques, such as a regression technique. An aggregate response variable may take the form of the logical disjunction (logical OR) of the response variables from each of the individual failure models. For example, aggregate response variables associated with any set of measurements that occur within any timeframe determined at block 706 may have a value of one, while aggregate response variables associated with sets of measurements that occur outside any of the timeframes may have a value of zero. Other manners of defining the health-metric model are also possible.

In some implementations, block 710 may be unnecessary. For example, as discussed above, the analytics system 108 may determine a single failure model, in which case the health-metric model may be the single failure model.

In practice, the analytics system 108 may be configured to update the individual failure models and/or the overall health-metric model. The analytics system 108 may update a model daily, weekly, monthly, etc. and may do so based on a new portion of historical operating data from the asset 102 or from other assets (e.g., from other assets in the same fleet as the asset 102). Other examples are also possible.

The unavailability model may take various other forms as well. For example, the unavailability model may predict an asset's ability of the asset to communicate in a mesh network (e.g., based on the asset's operating data). In another example, the unavailability model may predict whether the asset is going off-line (e.g., based on time of day, battery life, scheduled maintenance, or the like).

Returning back to FIG. 6, the analytics system 108 may also be configured to define individualized predictive models for assets, which may involve utilizing the aggregate, predictive model as a baseline. The individualization may be based on certain characteristics of assets. In this way, the analytics system 108 may provide a given asset a more accurate and robust predictive model compared to the aggregate predictive model.

In particular, at block 606, the analytics system 108 may be configured to decide whether to individualize the aggregate model defined at block 604 for a given asset, such as the asset 102. The analytics system 108 may carry out this decision in a number of manners.

In some cases, the analytics system 108 may be configured to define individualized predictive models by default. In other cases, the analytics system 108 may be configured to decide whether to define an individualized predictive model based on certain characteristics of the asset 102. For example, in some cases, only assets of certain types or classes, or operated in certain environments, or that have certain health scores may receive an individualized predictive model. In yet other cases, a user may define whether an individualized model is defined for the asset 102. Other examples are also possible.

In any event, if the analytics system 108 decides to define an individualized predictive model for the asset 102, the analytics system 108 may do so at block 608. Otherwise, the analytics system 108 may end the definition phase.

At block 608 the analytics system 108 may be configured to define an individualized predictive model in a number of manners. In example implementations, the analytics system 108 may define an individualized predictive model based at least in part on one or more characteristics of the asset 102.

Before defining the individualized predictive model for the asset 102, the analytics system 108 may have determined one or more asset characteristics of interest that form the basis of individualized models. In practice, different predictive models may have different corresponding characteristics of interest.

In general, the characteristics of interest may be characteristics that are related to the aggregate, predictive model. For instance, the characteristics of interest may be characteristics that the analytics system 108 has determined influence the accuracy of the aggregate, predictive model. Examples of such characteristics may include asset age, asset usage, asset capacity, asset load, asset health (perhaps indicated by an asset health metric, discussed below), asset class (e.g., brand and/or model), and environment in which an asset is operated, among other characteristics.

The analytics system 108 may have determined the characteristics of interest in a number of manners. In one example, the analytics system 108 may have done so by performing one or more modeling simulations that facilitate identifying the characteristics of interest. In another example, the characteristics of interest may have been predefined and stored in the data storage of the analytics system 108. In yet another example, characteristics of interest may have been defined by a user and provided to the analytics system 108 via the output system 110. Other examples are also possible.

In any event, after determining the characteristics of interest, the analytics system 108 may determine characteristics of the asset 102 that correspond to the determined characteristics of interest. That is, the analytics system 108 may determine a type, value, existence or lack thereof, etc. of the asset 102's characteristics that correspond to the characteristics of interest. The analytics system 108 may perform this operation in a number of manners.

For example, the analytics system 108 may be configured to perform this operation based on data originating from the asset 102 and/or the data source 112. In particular, the analytics system 108 may utilize operating data for the asset 102 and/or external data from the data source 112 to determine one or more characteristics of the asset 102. Other examples are also possible.

Based on the determined one or more characteristics of the asset 102, the analytics system 108 may define an individualized, predictive model by modifying the aggregate model. The aggregate model may be modified in a number of manners. For example, the aggregate model may be modified by changing (e.g., adding, removing, re-ordering, etc.) one or more model inputs, changing one or more sensor and/or actuator measurement ranges that correspond to asset-operating limits (e.g., changing operating limits that correspond to "leading indicator" events), changing one or more model calculations, weighting (or changing a weight of) a variable or output of a calculation, utilizing a modeling technique that differs from that which was utilized to define the aggregate model, and/or utilizing a response variable that differs from that which was utilized to define the aggregate model, among other examples.

In practice, individualizing the aggregate model may depend on the one or more characteristics of the given asset. In particular, certain characteristics may affect the modification of the aggregate model differently than other characteristics. Further, the type, value, existence, or the like of a characteristic may affect the modification as well. For example, the asset age may affect a first part of the aggregate model, while an asset class may affect a second, different part of the aggregate model. And an asset age within a first range of ages may affect the first part of the aggregate model in a first manner, while an asset age within a second range of ages, different from the first range, may affect the first part of the aggregate model in a second, different manner. Other examples are also possible.

In some implementations, individualizing the aggregate model may depend on considerations in addition to or alternatively to asset characteristics. For instance, the aggregate model may be individualized based on sensor and/or actuator readings of an asset when the asset is known to be in a relatively good operating state (e.g., as defined by a mechanic or the like). More particularly, in an example of a leading-indicator predictive model, the analytics system 108 may be configured to receive an indication that the asset is in a good operating state (e.g., from a computing device operated by a mechanic) along with operating data from the asset. Based at least on the operating data, the analytics system 108 may then individualize the leading-indicator predictive model for the asset by modifying respective operating limits corresponding to "leading indicator" events. Other examples are also possible.

It should also be understood that, in some example implementations, the analytics system 108 may be configured to define an individualized predictive model for a given asset without first defining an aggregate predictive model. Other examples are also possible.

2. Workflow for Updating a Routing Table

As noted above, the analytics system 108 may also be configured to define a workflow for causing a routing table to be updated based on an unavailability model. As described above, the analytics system 108 may execute an unavailability model to determine whether a given asset of a plurality of assets in a mesh network is likely to be unavailable within a given period of time in the future. The given asset may be unavailable based on a failure of the given asset, the given asset going off-line, a scheduled down time for the given asset, the given asset being unable to communicate over the mesh network, or the given asset otherwise being unable to function as a data relay in the mesh network, among other scenarios.

In any event, a workflow that updates a routing table may cause an asset serving as a node within a mesh network to update its routing information to account for one or multiple other assets likely becoming unavailable in the future. In this way, the mesh network may be prospectively updated so as to utilize paths that do not rely on a node (asset) that is likely to become unavailable in the future.

The analytics system 108 may define such a routing-table workflow so that it is triggered based on a variety of triggers. In general, such a trigger may indicate that a given asset is likely to be unavailable. In example implementations, a trigger may take the form of a health score of the given asset. Specifically, the routing-table workflow may be triggered based on the analytics system 108 (or perhaps a local analytics device of the given asset) determining that the given asset's health score meets, stays below, or exceeds an unavailability threshold (e.g., a health-score threshold value), which may depend on how the scoring is structured.

Alternatively, the trigger may be based on the analytics system 108 determining that the given asset's health score meets, stays below, or exceeds an unavailability threshold for a given period of time. For example, it may not be enough for the given asset to be momentarily unavailable; the given asset may be deemed to be unavailable if it is determined that the given asset will likely be unavailable for a particular amount of time, such as 30 minutes, one or multiple hours, etc. In example implementations, the analytics system 108 may determine the period of time of unavailability that triggers the workflow based on a comparison of recent throughput of a given route being analyzed and a minimum time needed to transmit a given message (e.g., of particular size) through the given route assuming those throughput conditions are present. The period of time may be determined in other manners as well.

In practice, the analytics system 108 may define the routing-table workflow with respect to all of the assets 102, 103, and 104 (e.g., an aggregate workflow). However, in some implementations, the analytics system 108 may individualize the workflow for one or more assets. For example, asset 102 may have a different unavailability threshold than that of asset 103.

The analytics system 108 may decide whether to define an individualized workflow based on the individualized predictive model. In yet another implementation, the analytics system 108 may decide to define an individualized workflow if an individualized predictive model was defined. In another implementation, the analytics system 108 may use characteristics of interest that affect the efficacy of the aggregate workflow to determine different unavailability thresholds for different assets. Other examples are also possible.

In operation, the analytics system 108 may transmit a signaling message to one or more of the assets 102-104 based on the executed workflow. That is, the signaling message may reflect the analytics system 108 determining that a given asset is likely to be unavailable within the given period of time in the future. The signaling message may instruct the asset to update its routing table to update the routing topology and may also instruct the asset to relay the update to other assets. For example, based on executing the unavailability model and determining that the asset 104 is likely to become unavailable, the analytics system 108 may transmit a signaling message to asset 102, which in turn updates its routing table. Asset 102 may subsequently transmit the signaling message to asset 103, which updates its routing table.

Moreover, in some implementations, the signaling message may include instructions to remove the soon to be unavailable asset (e.g., the asset 104) from the routing topology. In another implementation, the analytics system 108 may update the routing topology for each asset in the mesh network 105 and transmit an indication of the updated routing topology to each asset (e.g., via transmitting respective routing tables to the assets).

D. Execution of the Model-Workflow Pair

Once the model-workflow pair disclosed above is defined by the analytics system 108, that model-workflow pair could then be executed by the analytics system 108 and/or could be sent to an asset for local execution (e.g., by a local analytics device).

While executing an unavailability model, the analytics system 108 and/or a given asset may determine that the given asset is likely to become unavailable within a given period of time in the future. For instance, the analytics system 108 and/or a given asset may make this determination by comparing the output of the unavailability model to a threshold and thereby determining that the output has met or exceeded the threshold. In turn, the analytics system 108 and/or the given asset may execute the workflow for causing one or more routing tables to be updated. For instance, the analytics system 108 may transmit a signal message to one or more assets that includes a determination that a given asset is unlikely to be unavailable. In another example, the analytics system 108 may transmit a signal message to one or more assets that includes updates to a routing configuration for the respective asset.

As a result of executing this workflow, the soon-to-be unavailable asset may be removed from the routing table or the paths that include that asset may be disabled. For example, the routing table may be updated such that the other assets in the mesh network may route around the soon-to-be unavailable asset by presuming that it is unavailable.

The model-workflow pair disclosed herein may also cause the routing table to later be updated again if it determines that the soon-to-be unavailable asset becomes available again.

While the above discusses assets serving as nodes in a network, this is not intended to be limiting. In some example implementations, a sensor (e.g., an environmental sensor, industrial automation sensor, etc.) may serve as a node and above operations may be modified accordingly.

VI. Example Method

Figure 8:
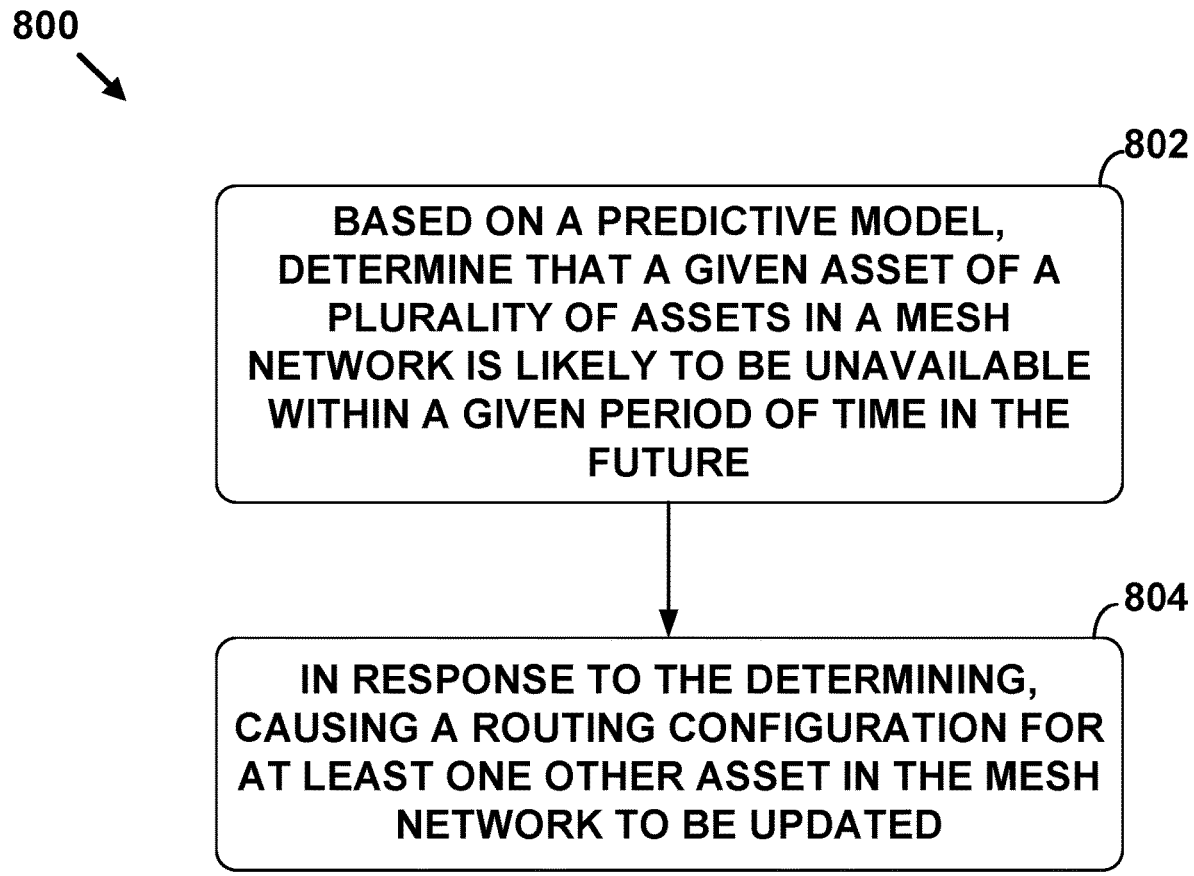
FIG. 8 depicts an example method to update a routing configuration for a mesh network.

FIG. 8 is a flow diagram 800 depicting an example method to update a routing table for a mesh network 105. For purposes of illustration, the example method is described as being carried out by the analytics system 108, but this definition phase may be carried out by other systems as well including a local analytics device 220 of one of the assets in the mesh network 105. One of ordinary skill in the art will appreciate that the flow diagram 500 is provided for sake of clarity and explanation and that numerous other combinations of operations may be utilized to update a routing table in a mesh network.

As shown in FIG. 8, at block 802, the analytics system 108 may begin by, based on a predictive model, determining that a given asset of a plurality of assets in a mesh network is likely to be unavailable within a given period of time in the future. In some implementations, the plurality of assets may include at least one of a transportation machine, an industrial machine, a medical machine, and a utility machine.

In some implementations, the predictive model may be based on historical data received from sensors for multiple assets. The analytics system 108 may determine that the given asset is likely to be unavailable based on receiving sensor data from the given asset or from other assets, determining a health score for the given asset based on applying the predictive model to the sensor data, and determining that the health score for the given asset has met an unavailability likelihood threshold. In some other implementations, the predictive model may be based on information associated with the asset. For example, the given asset may be unavailable based on a failure of the asset, a scheduled down time for the asset (e.g., the asset going off-line), the asset powering down for the night, and the asset being unable to communicate over the mesh network. The predictive model may determine that the given asset is likely to be unavailable based on an age of the asset, a total time in operation, a time since a last maintenance event, etc.

At block 804, in response to the determining, causing a routing configuration for at least one other asset in the mesh network to be updated. The routing configuration may include paths for each of the assets in the mesh network to transmit data to or receive data from one or more other assets and to other entities in the system described above with reference to FIG. 1.

The routing configuration may include removing assets from a routing table that are likely to become unavailable. Alternatively or additionally, the analytics system 108 may keep those assets as part of the routing table but may update paths that include the assets that are likely to become unavailable until a state of those assets changes. For example, where assets are associated with a health score, the assets might be determined to be available if the health score increases or falls below the unavailability likelihood threshold. In some implementations where an asset 200 updates the routing table for the mesh network, the asset may communicate based on the updated routing table and transmit at least a portion of the updated routing table to another of the plurality of the assets.

What is claimed is:

1. A computer-implemented method comprising:
    receiving, at a local analytics device coupled to a given asset that is part of a mesh network comprising a plurality of assets, operating data that is indicative of the operating conditions of the given asset, wherein the given asset is equipped with a respective set of sensors for monitoring the operating conditions of the given asset;
    executing, at the local analytics device, a predictive model that takes the received operating data for the given asset as inputs and outputs a likelihood value for the given asset indicating a likelihood that the given asset will become unavailable within a given period of time in the future;
    while executing the predictive model for the given asset, determining that the likelihood value for the given asset has met threshold criteria indicating that the given asset is likely to be unavailable within the given period of time in the future;
    in response to the determining, communicating with at least one other asset in the mesh network to cause a routing configuration for the at least one other asset to be updated such that the given asset is removed from the routing configuration.

2. The computer-implemented method of claim 1,
    wherein receiving the operating data for the given asset comprises receiving sensor data for the given asset;
    wherein executing the predictive model for the given asset comprises executing a health score model that takes the sensor data for the given asset as inputs and outputs a health score for the given asset indicating a likelihood that an operational failure will occur at the given asset within the given period of time in the future; and
    wherein determining that the likelihood value for the given asset has met threshold criteria indicating that the given asset is likely to be unavailable within the given period of time in the future comprises determining that the health score for the given asset has met threshold criteria indicating that the given asset is likely to have an operational failure within the given period of time in the future.

3. The computer-implemented method of claim 2, wherein determining that the health score for the given asset has met the threshold criteria comprises determining that the health score for the given asset has exceeded a health score threshold value for a certain period of time.

4. The computer-implemented method of claim 1, wherein determining that the likelihood value for the given asset has met threshold criteria indicating that the given asset is likely to become unavailable within the given period of time in the future comprises determining that the likelihood value for the given asset has met threshold criteria indicating that the given asset is likely to become unavailable due to at least one of a failure at the given asset, the given asset going off-line, a scheduled down time for the given asset, or the given asset being unable to communicate over the mesh network.

5. The computer-implemented method of claim 1, wherein the given asset comprises at least one of a transportation machine, an industrial machine, a medical machine, or a utility machine.

6. The computer-implemented method of claim 1, wherein communicating with at least one other asset in the mesh network to cause a routing configuration for the at least one other asset to be updated such that the given asset is removed from the routing configuration comprises:
    transmitting an indication that the given asset is likely to become unavailable within the given period of time in the future to the at least one other asset and thereby causing the at least one other asset in the mesh network to remove the given asset from the routing configuration.

7. The computer-implemented method of claim 1, wherein communicating with at least one other asset in the mesh network to cause a routing configuration for the at least one other asset to be updated such that the given asset is removed from the routing configuration comprises:
    updating the routing configuration for the mesh network by removing the given asset from the routing configuration; and
    transmitting the updated routing configuration to the at least one other asset.

8. A local analytics device comprising:
    an asset interface configured to couple the local analytics device to a given asset that is equipped with a respective set of sensors for monitoring the operating conditions of the given asset;
    a network interface configured to facilitate communication between the given asset and one or more other assets in a mesh network;
    at least one processor;
    a non-transitory computer-readable medium; and
    program instructions stored on the non-transitory computer-readable medium that are executable by the at least one processor to cause the local analytics device to:
        receive, via the asset interface, operating data that is indicative of the operating conditions of the given asset;
        execute a predictive model that takes the received operating data for the given asset as inputs and outputs a likelihood value for the given asset indicating a likelihood that the given asset will become unavailable within a given period of time in the future;

while executing the predictive model for the given asset, determine that the likelihood value for the given asset has met threshold criteria indicating that the given asset is likely to be unavailable within the given period of time in the future; and in response to the determination, communicate, via the network interface, with at least one other asset in the mesh network to cause a routing configuration for the at least one other asset to be updated such that the given asset is removed from the routing configuration.

9. The local analytics device of claim 8,
wherein the program instructions that are executable by the at least one processor to cause the local analytics device to receive the operating data for the given asset comprise program instructions stored on the non-transitory computer-readable medium that are executable by the at least one processor to cause the local analytics device to receive sensor data for the given asset;
wherein the program instructions that are executable by the at least one processor to cause the local analytics device to execute the predictive model for the given asset comprise program instructions stored on the non-transitory computer-readable medium that are executable by the at least one processor to cause the local analytics device to execute a health score model that takes the sensor data for the given asset as inputs and outputs a health score for the given asset indicating a likelihood that an operational failure will occur at the given asset within the given period of time in the future; and
wherein the program instructions that are executable by the at least one processor to cause the local analytics device to determine that the likelihood value for the given asset has met threshold criteria indicating that the given asset is likely to be unavailable within the given period of time in the future comprise program instructions stored on the non-transitory computer-readable medium that are executable by the at least one processor to cause the local analytics device to determine that the health score for the given asset has met threshold criteria indicating that the given asset is likely to have an operational failure within the given period of time in the future.

10. The local analytics device of claim 9, wherein the program instructions that are executable by the at least one processor to cause the local analytics device to determine that the health score for the given asset has met the threshold criteria comprise program instructions stored on the non-transitory computer-readable medium that are executable by the at least one processor to cause the local analytics device to determine that the health score for the given asset has exceeded a health score threshold value for a certain period of time.

11. The computing system of claim 8, wherein the program instructions that are executable by the at least one processor to cause the local analytics device to determine that the likelihood value for the given asset has met threshold criteria indicating that the given asset is likely to become unavailable within the given period of time in the future comprise program instructions stored on the non-transitory computer-readable medium that are executable by the at least one processor to cause the local analytics device to determine that the likelihood value for the given asset has met threshold criteria indicating that the given asset is likely to become unavailable due to at least one of a failure at the given asset, the given asset going off-line, a scheduled down time for the given asset, or the given asset being unable to communicate over the mesh network.

12. The local analytics device of claim 8, wherein the given asset comprises at least one of a transportation machine, an industrial machine, a medical machine, or a utility machine.

13. The local analytics device of claim 8, wherein the program instructions that are executable by the at least one processor to cause the local analytics device to communicate with at least one other asset in the mesh network to cause a routing configuration for the at least one other asset to be updated such that the given asset is removed from the routing configuration comprise program instructions stored on the non-transitory computer-readable medium that are executable by the at least one processor to cause the local analytics device to:
transmit an indication that the given asset is likely to become unavailable within the given period of time in the future to the at least one other asset and thereby causing the at least one other asset in the mesh network to remove the given asset from the routing configuration.

14. A non-transitory computer-readable medium having instructions stored thereon that are executable to cause a computing system to:
receive, via an asset interface, operating data that is indicative of the operating conditions of a given asset that is part of a mesh network comprising a plurality of assets, wherein the given asset is equipped with a respective set of sensors for monitoring the operating conditions of the given asset;
execute a predictive model that takes the received operating data for the given asset as inputs and outputs a likelihood value for the given asset indicating a likelihood that the given asset will become unavailable within a given period of time in the future;
while executing the predictive model for the given asset, determine that the likelihood value for the given asset has met threshold criteria indicating that the given asset is likely to be unavailable within the given period of time in the future; and
in response to the determination, communicate with at least one other asset in the mesh network to cause a routing configuration for the at least one other asset to be updated such that the given asset is removed from the routing configuration.

15. The computer-readable medium of claim 14,
wherein the instructions that are executable to cause the computing system to receive the operating data for the given asset comprise instructions that are executable to cause the computing system to receive sensor data for the given asset;
wherein the instructions that are executable to cause the computing system to execute the predictive model for the given asset comprise instructions that are executable to cause the computing system to execute a health score model that takes the sensor data for the given asset as inputs and outputs a health score for the given asset indicating a likelihood that an operational failure will occur at the given asset within the given period of time in the future; and
wherein the instructions that are executable to cause the computing system to determine that the health score for the given asset has met the threshold criteria comprise instructions that are executable to cause the computing system to determine that the health score for the given asset has met threshold criteria indicating that the given asset is likely to have an operational failure within the given period of time in the future.

16. The computer-readable medium of claim 15, wherein the instructions that are executable to cause the computing system to determine that the health score for the given asset has met the threshold criteria comprise instructions that are executable to cause the computing system to determine that the health score for the given asset has met threshold criteria indicating that the given asset is likely to become unavailable due to at least one of a failure at the given asset, the given asset going off-line, a scheduled down time for the given asset, or the given asset being unable to communicate over the mesh network.

17. The computer-readable medium of claim 14, wherein the instructions that are executable to cause the computing system to determine that the likelihood value for the given asset has met threshold criteria indicating that the given asset is likely to become unavailable within the given period of time in the future comprise instructions that are executable to cause the computing system to determine that the likelihood value for the given asset has met threshold criteria indicating that the given asset is likely to become unavailable due to at least one of a failure at the given asset, the given asset going off-line, a scheduled down time for the given asset, or the given asset being unable to communicate over the mesh network.

18. The computer-readable medium of claim 14, wherein the given asset comprises at least one of a transportation machine, an industrial machine, a medical machine, or a utility machine.

19. The computer-readable medium of claim 14, wherein the instructions that are executable to cause the computing system to communicate with at least one other asset in the mesh network to cause a routing configuration for the at least one other asset to be updated such that the given asset is removed from the routing configuration comprise instructions that are executable to cause the computing system to:

transmit an indication that the given asset is likely to become unavailable within the given period of time in the future to the at least one other asset and thereby causing the at least one other asset in the mesh network to remove the given asset from the routing configuration.

20. The computer-readable medium of claim 14, wherein the instructions that are executable to cause the computing system to communicate with at least one other asset in the mesh network to cause a routing configuration for the at least one other asset to be updated such that the given asset is removed from the routing configuration comprise instructions that are executable to cause the computing system to:

update the routing configuration for the mesh network by removing the given asset from the routing configuration; and transmit the updated routing configuration to the at least one other asset.

\* \* \* \* \*